(12) United States Patent
Schaeffer et al.

(10) Patent No.: US 9,974,563 B2
(45) Date of Patent: May 22, 2018

(54) MEDICAL DEVICES HAVING A RELEASABLE MEMBER AND METHODS OF USING THE SAME

(71) Applicant: Cook Medical Technologies LLC, Bloomington, IN (US)

(72) Inventors: Darin Schaeffer, Bloomington, IN (US); Kathryn Hardert, Bloomington, IN (US); Joshua Haines, West Chester, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 44 days.

(21) Appl. No.: 14/721,618

(22) Filed: May 26, 2015

(65) Prior Publication Data
US 2015/0342636 A1    Dec. 3, 2015

Related U.S. Application Data

(60) Provisional application No. 62/003,700, filed on May 28, 2014.

(51) Int. Cl.
*A61B 17/34*    (2006.01)
*A61M 25/06*    (2006.01)
*A61M 39/10*    (2006.01)
*A61M 39/02*    (2006.01)
*A61B 17/00*    (2006.01)

(52) U.S. Cl.
CPC ..... *A61B 17/3421* (2013.01); *A61M 25/0662* (2013.01); *A61M 39/02* (2013.01); *A61M 39/1055* (2013.01); *A61B 2017/00477* (2013.01); *A61B 2017/345* (2013.01)

(58) Field of Classification Search
CPC ...... A61B 17/3421; A61B 2017/00477; A61B 2017/345; A61M 25/0662; A61M 39/02; A61M 39/1055
See application file for complete search history.

(56) References Cited

U.S. PATENT DOCUMENTS

| | | |
|---|---|---|
| 3,663,965 A | 5/1972 | Lee, Jr. et al. |
| 3,818,511 A | 6/1974 | Goldberg et al. |
| 4,024,859 A | 5/1977 | Slepyan et al. |

(Continued)

FOREIGN PATENT DOCUMENTS

| | | |
|---|---|---|
| EP | 0577400 | 1/1994 |
| EP | 1159924 | 12/2001 |

(Continued)

OTHER PUBLICATIONS

International Searching Authority, "IPER," for Int. App. No. PCT/US2014/049589, dated Feb. 18, 2016, pp. 1-13.

(Continued)

*Primary Examiner* — Lauren P Farrar
(74) *Attorney, Agent, or Firm* — Buchanan Van Tuinen LLC

(57) ABSTRACT

Medical devices having a releasable member are described. Methods of using medical devices having a releasable member are also described. An example medical device comprises an elongate member, an intermediate member, a sheath, and a cap. Each of the intermediate member, sheath, and cap are releasably disposed on the elongate member.

20 Claims, 6 Drawing Sheets

(56) References Cited

U.S. PATENT DOCUMENTS

| | | | |
|---|---|---|---|
| 4,064,873 A | 12/1977 | Swenson | |
| 4,217,664 A | 8/1980 | Faso | |
| 4,338,937 A | 7/1982 | Lerman | |
| 4,449,974 A | 5/1984 | Messingschlager | |
| 4,608,972 A | 9/1986 | Small | |
| 4,623,348 A | 11/1986 | Feit | |
| 4,753,656 A | 6/1988 | Tofield et al. | |
| 4,917,604 A | 4/1990 | Small | |
| 5,084,064 A | 1/1992 | Barak et al. | |
| 5,117,839 A * | 6/1992 | Dance | A61M 25/0136 600/434 |
| 5,129,887 A * | 7/1992 | Euteneuer | A61M 25/104 604/533 |
| 5,176,649 A | 1/1993 | Wakabayashi | |
| 5,304,142 A | 4/1994 | Liebl et al. | |
| 5,308,318 A | 5/1994 | Plassche, Jr. | |
| 5,389,088 A | 2/1995 | Hageman | |
| 5,425,761 A | 6/1995 | Lundgren | |
| 5,477,860 A | 12/1995 | Essen-Moller | |
| 5,489,278 A | 2/1996 | Abrahamson | |
| 5,674,191 A | 10/1997 | Edwards et al. | |
| 5,715,840 A | 2/1998 | Hall | |
| 5,782,807 A | 7/1998 | Falvai et al. | |
| 5,830,195 A | 11/1998 | Peters et al. | |
| 5,951,518 A | 9/1999 | Licata et al. | |
| 5,954,050 A | 9/1999 | Christopher | |
| 5,974,724 A | 9/1999 | Frantz et al. | |
| 5,988,171 A | 11/1999 | Sohn et al. | |
| 6,159,158 A | 12/2000 | Lowe | |
| 6,159,179 A | 12/2000 | Simonson | |
| 6,159,208 A | 12/2000 | Hovda et al. | |
| 6,397,841 B1 | 6/2002 | Kenyon et al. | |
| 6,408,851 B1 | 6/2002 | Karell | |
| 6,505,625 B1 | 1/2003 | Uenishi | |
| 6,513,530 B2 | 2/2003 | Knudson et al. | |
| 6,513,531 B2 | 2/2003 | Knudson et al. | |
| 6,523,541 B2 | 2/2003 | Knudson et al. | |
| 6,527,737 B2 | 3/2003 | Kaneshige | |
| 6,536,424 B2 | 3/2003 | Fitton | |
| 6,536,439 B1 | 3/2003 | Palmisano | |
| 6,585,703 B1 | 7/2003 | Kassel et al. | |
| 6,619,290 B1 | 9/2003 | Zacco | |
| 6,764,464 B2 | 7/2004 | McGuckin, Jr. et al. | |
| 6,895,963 B1 | 5/2005 | Martin et al. | |
| 6,910,483 B2 | 6/2005 | Daly et al. | |
| 6,955,172 B2 | 10/2005 | Nelson et al. | |
| 6,966,319 B2 | 11/2005 | Fitton | |
| 6,974,419 B1 | 12/2005 | Voss et al. | |
| 7,004,172 B1 | 2/2006 | Zacco | |
| 7,004,941 B2 | 2/2006 | Tvinnereim et al. | |
| 7,037,290 B2 | 5/2006 | Gardeski et al. | |
| 7,047,979 B2 | 5/2006 | Conrad et al. | |
| 7,063,089 B2 | 6/2006 | Knudson et al. | |
| 7,073,505 B2 | 7/2006 | Nelson et al. | |
| 7,090,672 B2 | 8/2006 | Underwood et al. | |
| 7,128,069 B2 | 10/2006 | Farrugia et al. | |
| 7,168,429 B2 | 1/2007 | Matthews et al. | |
| 7,188,627 B2 | 3/2007 | Nelson et al. | |
| 7,195,646 B2 | 3/2007 | Nahleili | |
| 7,213,599 B2 | 5/2007 | Conrad et al. | |
| 7,216,647 B2 | 5/2007 | Lang et al. | |
| 7,232,462 B2 | 6/2007 | Schaeffer | |
| 7,255,109 B2 | 8/2007 | Knudson et al. | |
| 7,269,453 B2 | 9/2007 | Mogul | |
| 7,291,112 B2 | 11/2007 | Martin et al. | |
| 7,337,778 B2 | 3/2008 | Martin et al. | |
| 7,337,781 B2 | 3/2008 | Vassallo | |
| 7,360,542 B2 | 4/2008 | Nelson et al. | |
| 7,363,926 B2 | 4/2008 | Pflueger et al. | |
| 7,387,634 B2 | 6/2008 | Benderev | |
| 7,401,611 B2 | 7/2008 | Conrad et al. | |
| 7,491,200 B2 | 2/2009 | Underwood | |
| 7,507,258 B2 | 3/2009 | Nahleili | |
| 7,607,439 B2 | 10/2009 | Li | |
| 7,644,714 B2 | 1/2010 | Atkinson et al. | |
| 7,658,192 B2 | 2/2010 | Harrington | |
| 7,669,603 B2 | 3/2010 | Knudson et al. | |
| 7,673,635 B2 | 3/2010 | Conrad et al. | |
| 7,680,538 B2 | 3/2010 | Durand et al. | |
| 7,703,460 B2 | 4/2010 | Conrad et al. | |
| 7,731,708 B2 | 6/2010 | Haarala et al. | |
| 7,762,991 B2 | 7/2010 | Bierman et al. | |
| 7,766,926 B2 | 8/2010 | Bosley, Jr. et al. | |
| 7,770,582 B2 | 8/2010 | Chen et al. | |
| 7,789,843 B2 | 9/2010 | Ray | |
| 7,793,661 B2 | 9/2010 | Macken | |
| 7,798,149 B2 | 9/2010 | Haduong | |
| 7,810,502 B1 | 10/2010 | Nguyen et al. | |
| 7,810,503 B2 | 10/2010 | Magnin | |
| 7,813,812 B2 | 10/2010 | Kieval et al. | |
| 7,819,122 B2 | 10/2010 | Abramson | |
| 7,827,038 B2 | 11/2010 | Richard et al. | |
| 7,827,988 B2 | 11/2010 | Matthews et al. | |
| 7,827,991 B2 | 11/2010 | Maher | |
| 7,832,402 B2 | 11/2010 | Nelissen | |
| 7,832,403 B2 | 11/2010 | Halstrom et al. | |
| 7,836,888 B2 | 11/2010 | Hegde et al. | |
| 7,836,889 B2 | 11/2010 | Kusukawa | |
| 7,845,356 B2 | 12/2010 | Paraschac et al. | |
| 7,845,357 B2 | 12/2010 | Buscemi et al. | |
| 7,856,979 B2 | 12/2010 | Doshi et al. | |
| 7,856,980 B2 | 12/2010 | Lang et al. | |
| 7,861,722 B2 | 1/2011 | Keropian | |
| 7,861,723 B2 | 1/2011 | Dedrick et al. | |
| 7,861,724 B2 | 1/2011 | Keropian | |
| 7,862,721 B2 | 1/2011 | Bergersen | |
| 7,870,860 B2 | 1/2011 | McCormick et al. | |
| 7,874,291 B2 | 1/2011 | Ging et al. | |
| 7,874,294 B2 | 1/2011 | Burger | |
| 7,884,101 B2 | 2/2011 | Teegarden et al. | |
| 7,909,037 B2 | 3/2011 | Hegde et al. | |
| 7,909,038 B2 | 3/2011 | Hegde et al. | |
| 7,918,228 B2 | 4/2011 | Smernoff | |
| 7,921,850 B2 | 4/2011 | Nelson et al. | |
| 7,934,506 B2 | 5/2011 | Woodson et al. | |
| 7,935,065 B2 | 5/2011 | Martin et al. | |
| 7,938,114 B2 | 5/2011 | Matthews et al. | |
| 7,949,400 B2 | 5/2011 | Kieval et al. | |
| 7,954,494 B1 | 6/2011 | Connor | |
| 7,954,496 B2 | 6/2011 | Jansheski et al. | |
| 7,955,267 B2 | 6/2011 | Voss et al. | |
| 7,958,895 B2 | 6/2011 | Nelson et al. | |
| 7,958,896 B2 | 6/2011 | Nelson et al. | |
| 7,959,554 B2 | 6/2011 | McAlexander et al. | |
| 7,971,591 B2 | 7/2011 | Jansheski | |
| 7,975,700 B2 | 7/2011 | Frazier et al. | |
| 7,975,701 B2 | 7/2011 | Bergersen | |
| 7,976,471 B2 | 7/2011 | Martin et al. | |
| 7,980,248 B2 | 7/2011 | Hegde et al. | |
| 7,984,714 B2 | 7/2011 | Hausmann et al. | |
| 7,987,854 B2 | 8/2011 | Arni | |
| 7,992,564 B2 | 8/2011 | Doshi et al. | |
| 7,992,566 B2 | 8/2011 | Pflueger et al. | |
| 7,992,567 B2 | 8/2011 | Hirotsuka et al. | |
| 7,997,266 B2 | 8/2011 | Frazier et al. | |
| 7,997,267 B2 | 8/2011 | Ging et al. | |
| 7,997,276 B2 | 8/2011 | Goff | |
| 8,001,971 B2 | 8/2011 | Boucher et al. | |
| 8,001,972 B2 | 8/2011 | Eubank | |
| 8,001,973 B2 | 8/2011 | Solos et al. | |
| 8,015,975 B2 | 9/2011 | Zohlmann, Jr. | |
| 8,020,560 B2 | 9/2011 | Paraschac et al. | |
| 8,025,063 B2 | 9/2011 | Sotos et al. | |
| 8,026,405 B2 | 9/2011 | Beaudry | |
| 8,028,703 B1 | 10/2011 | Moses | |
| 8,033,282 B2 | 10/2011 | Eubank | |
| 8,037,885 B2 | 10/2011 | Metzger et al. | |
| 8,037,886 B2 | 10/2011 | Solos et al. | |
| 8,047,201 B2 | 11/2011 | Guyuron et al. | |
| 8,047,206 B2 | 11/2011 | Boucher et al. | |
| 8,052,646 B2 | 11/2011 | Schweikert et al. | |
| 8,070,693 B2 | 12/2011 | Ayala et al. | |
| 8,074,655 B2 | 12/2011 | Sanders | |
| 8,096,303 B2 | 1/2012 | Dineen et al. | |

(56) References Cited

U.S. PATENT DOCUMENTS

| | | |
|---|---|---|
| 8,147,456 B2 | 4/2012 | Fisher et al. |
| 8,167,787 B2 | 5/2012 | Gillis |
| 8,220,466 B2 | 7/2012 | Frazier et al. |
| 8,220,467 B2 | 7/2012 | Sanders |
| 8,327,854 B2 | 12/2012 | Gillis et al. |
| 8,414,537 B2 | 4/2013 | Nardeo et al. |
| 8,425,466 B2 | 4/2013 | Sargent, Jr. |
| 8,460,322 B2 | 6/2013 | van der Burg et al. |
| 8,529,544 B2 | 9/2013 | Haarala et al. |
| 8,535,310 B2 | 9/2013 | Hardin, Jr. et al. |
| 8,535,349 B2 | 9/2013 | Chen et al. |
| 8,603,185 B2 | 12/2013 | Shah et al. |
| 2001/0050085 A1 | 12/2001 | Knudson et al. |
| 2003/0111079 A1 | 6/2003 | Matthews et al. |
| 2003/0140925 A1 | 7/2003 | Sapienza et al. |
| 2003/0168064 A1 | 9/2003 | Daly et al. |
| 2004/0028676 A1 | 2/2004 | Klein et al. |
| 2004/0073272 A1 | 4/2004 | Knudson et al. |
| 2004/0099275 A1 | 5/2004 | Zacco |
| 2004/0112387 A1 | 6/2004 | Lang et al. |
| 2004/0153127 A1 | 8/2004 | Gordon et al. |
| 2004/0187870 A1 | 9/2004 | Matthews et al. |
| 2005/0005937 A1 | 1/2005 | Farrugia et al. |
| 2005/0098184 A1 | 5/2005 | Conrad et al. |
| 2005/0103339 A1 | 5/2005 | Daly et al. |
| 2005/0126563 A1 | 6/2005 | van der Burg et al. |
| 2005/0217673 A1 | 10/2005 | Daly et al. |
| 2005/0256452 A1 | 11/2005 | Demarchi et al. |
| 2005/0267547 A1 | 12/2005 | Knudson et al. |
| 2005/0268914 A1 | 12/2005 | Paoluccio et al. |
| 2005/0279365 A1 | 12/2005 | Armijo et al. |
| 2006/0000475 A1 | 1/2006 | Matthews et al. |
| 2006/0070626 A1 | 4/2006 | Frazier et al. |
| 2006/0112962 A1 | 6/2006 | Tebbutt et al. |
| 2006/0150986 A1 | 7/2006 | Roue et al. |
| 2006/0169289 A1 | 8/2006 | Zacco |
| 2006/0201519 A1 | 9/2006 | Frazier et al. |
| 2006/0201520 A1 | 9/2006 | Christensen, III |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0235264 A1 | 10/2006 | Vassallo |
| 2006/0235877 A1 | 10/2006 | Richard et al. |
| 2006/0263145 A1 | 11/2006 | Pal et al. |
| 2007/0016166 A1 | 1/2007 | Thistle |
| 2007/0132117 A1 | 6/2007 | Truitt et al. |
| 2007/0134085 A1 | 6/2007 | Daly et al. |
| 2007/0144539 A1 | 6/2007 | van der Burg et al. |
| 2007/0157928 A1 | 7/2007 | Pujol et al. |
| 2007/0157934 A1 | 7/2007 | Lang et al. |
| 2007/0207994 A1 | 9/2007 | Teegarden et al. |
| 2007/0209664 A1 | 9/2007 | Paraschac et al. |
| 2007/0209665 A1 | 9/2007 | Gillis et al. |
| 2007/0244086 A1 | 10/2007 | Teegarden et al. |
| 2007/0256693 A1 | 11/2007 | Paraschac et al. |
| 2007/0287923 A1 | 12/2007 | Adkins et al. |
| 2008/0023012 A1 | 1/2008 | Dineen et al. |
| 2008/0027480 A1 | 1/2008 | van der Burg et al. |
| 2008/0027560 A1 | 1/2008 | Jackson et al. |
| 2008/0035160 A1 | 2/2008 | Woodson et al. |
| 2008/0041382 A1 | 2/2008 | Matthews et al. |
| 2008/0041383 A1 | 2/2008 | Matthews et al. |
| 2008/0041398 A1 | 2/2008 | Hegde et al. |
| 2008/0045813 A1 | 2/2008 | Phuah et al. |
| 2008/0053461 A1 | 3/2008 | Hirotsuka et al. |
| 2008/0058584 A1 | 3/2008 | Hirotsuka et al. |
| 2008/0066753 A1 | 3/2008 | Martin et al. |
| 2008/0066765 A1 | 3/2008 | Paraschac et al. |
| 2008/0066769 A1 | 3/2008 | Dineen et al. |
| 2008/0097380 A1 | 4/2008 | Li |
| 2008/0099019 A1 | 5/2008 | Martin et al. |
| 2008/0115791 A1 | 5/2008 | Heine |
| 2008/0194953 A1 | 8/2008 | Kerber |
| 2008/0208265 A1 | 8/2008 | Frazier et al. |
| 2008/0251071 A1 | 10/2008 | Armitstead et al. |
| 2008/0306442 A1 | 12/2008 | Bardsley et al. |
| 2009/0044814 A1 | 2/2009 | Iancea et al. |
| 2009/0053306 A1 | 2/2009 | Agarwal et al. |
| 2009/0060905 A1 | 3/2009 | Martin et al. |
| 2009/0088599 A1 | 4/2009 | Zook et al. |
| 2009/0099471 A1 | 4/2009 | Broadley et al. |
| 2009/0131923 A1 | 5/2009 | Connors et al. |
| 2010/0004264 A1 | 1/2010 | Xiang et al. |
| 2010/0010061 A1 | 1/2010 | Cooper et al. |
| 2010/0016694 A1 | 1/2010 | Martin et al. |
| 2010/0028026 A1 | 2/2010 | Lnami et al. |
| 2010/0106246 A1 | 4/2010 | Rousseau et al. |
| 2010/0108066 A1 | 5/2010 | Martin et al. |
| 2010/0108077 A1 | 5/2010 | Lindh et al. |
| 2010/0132719 A1 | 6/2010 | Jacobs et al. |
| 2010/0144701 A1 | 6/2010 | Cooper et al. |
| 2010/0234946 A1 | 9/2010 | Rousseau |
| 2010/0286793 A1 | 11/2010 | Newman et al. |
| 2010/0300458 A1 | 12/2010 | Stubbs et al. |
| 2011/0005526 A1 | 1/2011 | Garabadian et al. |
| 2011/0005529 A1 | 1/2011 | Doshi et al. |
| 2011/0005530 A1 | 1/2011 | Doshi et al. |
| 2011/0017220 A1 | 1/2011 | Lindsay et al. |
| 2011/0030700 A1 | 2/2011 | Wilson |
| 2011/0030701 A1 | 2/2011 | Lang et al. |
| 2011/0036357 A1 | 2/2011 | Abramson |
| 2011/0046712 A1 | 2/2011 | Melsheimer et al. |
| 2011/0048430 A1 | 3/2011 | Arnon |
| 2011/0048431 A1 | 3/2011 | Li |
| 2011/0056498 A1 | 3/2011 | Lang et al. |
| 2011/0067708 A1 | 3/2011 | Doshi et al. |
| 2011/0067709 A1 | 3/2011 | Doshi et al. |
| 2011/0073119 A1 | 3/2011 | Chen et al. |
| 2011/0088701 A1 | 4/2011 | Thornton |
| 2011/0092910 A1 | 4/2011 | Schultz |
| 2011/0094520 A1 | 4/2011 | Mikhailenok et al. |
| 2011/0100376 A1 | 5/2011 | Rousseau |
| 2011/0100378 A1 | 5/2011 | Rousseau |
| 2011/0108041 A1 | 5/2011 | Sather et al. |
| 2011/0114099 A1 | 5/2011 | Goldstein |
| 2011/0120476 A1 | 5/2011 | Keropian |
| 2011/0130249 A1 | 6/2011 | Mikhailenok et al. |
| 2011/0132378 A1 | 6/2011 | Levendowski et al. |
| 2011/0155142 A1 | 6/2011 | Boucher et al. |
| 2011/0155143 A1 | 6/2011 | Shantha |
| 2011/0155144 A1 | 6/2011 | Toussaint |
| 2011/0162658 A1 | 7/2011 | Fisher et al. |
| 2011/0166673 A1 | 7/2011 | Patel et al. |
| 2011/0168186 A1 | 7/2011 | Halstrom |
| 2011/0168187 A1 | 7/2011 | Nelissen |
| 2011/0168188 A1 | 7/2011 | Moore et al. |
| 2011/0174315 A1 | 7/2011 | Zhang et al. |
| 2011/0178439 A1 | 7/2011 | Irwin et al. |
| 2011/0180075 A1 | 7/2011 | Chen et al. |
| 2011/0180076 A1 | 7/2011 | Hegde et al. |
| 2011/0183928 A1 | 7/2011 | Thede et al. |
| 2011/0192404 A1 | 8/2011 | Chen |
| 2011/0203598 A1 | 8/2011 | Favet et al. |
| 2011/0214678 A1 | 9/2011 | Zhang et al. |
| 2011/0218451 A1 | 9/2011 | Lai et al. |
| 2011/0220123 A1 | 9/2011 | Robson |
| 2011/0220124 A1 | 9/2011 | Vaska et al. |
| 2011/0220125 A1 | 9/2011 | Van Dyke et al. |
| 2011/0226261 A1 | 9/2011 | Hernandez |
| 2011/0226262 A1 | 9/2011 | Gillis et al. |
| 2011/0226263 A1 | 9/2011 | Gillis et al. |
| 2011/0226264 A1 | 9/2011 | Friedman et al. |
| 2011/0232651 A1 | 9/2011 | Diers |
| 2011/0232652 A1 | 9/2011 | Levendowski et al. |
| 2011/0240037 A1 | 10/2011 | Hegde et al. |
| 2011/0240038 A1 | 10/2011 | Doshi et al. |
| 2011/0245850 A1 | 10/2011 | van der Burg et al. |
| 2011/0259345 A1 | 10/2011 | Cullen |
| 2011/0259346 A1 | 10/2011 | Tsuiki et al. |
| 2011/0265801 A1 | 11/2011 | Cullen |
| 2011/0265802 A1 | 11/2011 | Ha |
| 2011/0308530 A1 | 12/2011 | Gillis et al. |
| 2012/0162401 A1 | 6/2012 | Melder et al. |

(56) References Cited

U.S. PATENT DOCUMENTS

| | | | |
|---|---|---|---|
| 2012/0226341 A1* | 9/2012 | Schreck | A61F 2/966 623/1.12 |
| 2012/0265055 A1 | 10/2012 | Melsheimer et al. | |
| 2013/0041314 A1 | 2/2013 | Dillon | |
| 2013/0046138 A1 | 2/2013 | McLawhorn | |
| 2013/0056009 A1 | 3/2013 | Mohan et al. | |
| 2013/0060267 A1 | 3/2013 | Farnan et al. | |
| 2013/0085546 A1 | 4/2013 | Bolea et al. | |
| 2013/0123705 A1 | 5/2013 | Holm et al. | |
| 2013/0180528 A1 | 7/2013 | Zhou et al. | |
| 2013/0213409 A1 | 8/2013 | Podmore et al. | |
| 2013/0226146 A1 | 8/2013 | Tekulye | |
| 2013/0237967 A1 | 9/2013 | Schaeffer et al. | |
| 2013/0237968 A1 | 9/2013 | Schaeffer et al. | |
| 2013/0238003 A1 | 9/2013 | Fischer et al. | |
| 2013/0245662 A1 | 9/2013 | Schaeffer et al. | |
| 2014/0102460 A1 | 4/2014 | Catalano | |

FOREIGN PATENT DOCUMENTS

| | | |
|---|---|---|
| EP | 1501447 | 3/2009 |
| WO | WO199734649 | 9/1997 |
| WO | WO199850093 | 11/1998 |
| WO | WO2003075794 | 9/2003 |
| WO | WO2005056079 | 6/2005 |
| WO | WO2007056583 | 5/2007 |
| WO | WO2007149469 | 12/2007 |
| WO | WO2009140197 | 11/2009 |
| WO | WO2010045546 | 4/2010 |
| WO | WO2010051195 | 5/2010 |
| WO | WO2011068952 | 6/2011 |
| WO | WO2011123714 | 10/2011 |
| WO | WO2013010169 | 1/2013 |
| WO | WO2014189540 | 11/2014 |
| WO | WO2015020953 | 2/2015 |

OTHER PUBLICATIONS

The International Bureau of WIPO, International Preliminary Report on Patentability for application No. PCT/US2015/032577, dated Dec. 8, 2016, pp. 1-6.

International Searching Authority, International Search Report and Written Opinion for International application No. PCT/US2015/032577, dated Aug. 5, 2015, pp. 1-10.

File history of U.S. Appl. No. 08/883,220, now U.S. Pat. No. 5,988,171, as of Jun. 3, 2014. filed Jun. 26, 1997. First Named Inventor, Ze'ev Sohn. Title, Methods and Devices for the Treatment of Airway Obstruction, Sleep Apnea and Snoring.

File history of U.S. Appl. No. 10/877,003, now U.S. Pat. No. 7,213,599, as of Jun. 3, 2014. filed Jun. 24, 2004. First Named Inventor, Timothy R. Conrad. Title, Airway Implant.

File history of U.S. Appl. No. 11/757,501, now U.S. Pat. No. 7,703,460, as of Jun. 3, 2014. filed Jun. 4, 2007. First Named Inventor, Timothy R. Conrad. Title, Tongue Implant.

File history of U.S. Appl. No. 12/214,084 as of Jun. 3, 2014. filed Jun. 17, 2008. First Named Inventor, Octavian Iancea. Title, Implantable devices, systems, and methods for maintaining desired orientations in targeted tissue regions.

Woodson et al, "Multicenter study of a novel adjustable tongue-advancement device for obstructive sleep apnea," Otolaryngology and Head and Neck Surgery, Jun. 10, 2010, pp. 585-590, 143(4), Sage Publications.

Woodson et al, "Response to: Multicenter study of a novel adjustable tongue-advancement device for obstructive sleep apnea," Otolaryngology and Head and Neck Surgery, 211, pp. 1009-1010, 144(6), Sage Publications.

Hamans et al, "A novel tongue implant for tongue advancement for obstructive sleep apnea: Feasibility, safety and histology in a canine model," Journal of Musculoskeletal and Neuronal Interactions, Dec. 29, 2009, pp. 100-111, 10(1), Hylonome.

Kezirian, Eric J., M.D.,M.P.H., "Drug-Induced Sleepy Endoscopy," Dr. Kezirian's Blog, pp. 1-3, http://www.sleep-doctor.com/surgical-treatment-overview/drug-induced-sleep-endoscopy/, 2009-2014.

Medical News Today, "Aspire Medical Announces First Implant in US and Start of Clinical Trial to Treat Sleep Apnea," www.medicalnewstoday.com, May 23, 2007.

Park, Dr. Steven Y., "Aspire Medical Advance System for obstructive sleep apnea," Dr. Park: Breathe better, sleep better, live better. pp. 1-4. Oct. 6, 2010. <http://doctorstevenpark.com/aspire-medical-advance-system-for-obstructive-sleep-apnea>.

PR Newswire, "Aspire Medical appoints Roseanne Varner as president and CEO [press release]," pp. 1-2. May 1, 2011. <http://www.prnewswire.com/news-releases/aspire-medical-appoints-roseanne-varner-as-president-and-ceo-57760852.html>.

Siesta Medical, "Siesta Medical Receives 510(k) Clearance for Encore System to treat Obstructive Sleep Apnea," Siesta Medical, Los Gatos, CA, Sep. 12, 2011.

Revent Medical, "The Revent Solution: Tongue Implanter Kit," 2014. pp. 1-2, Retrieved Aug. 12, 2014. <http://www.reventmedical.com/solution/>.

Revent Medical, "The Revent Solution: Implant," 2014. pp. 1-2, Retrieved Aug. 12, 2014. <www.reventmedical.com/solution/>.

Knobbe, Martens, Olson & Bear, LLP, "Amendment and response to non-Final Office Action dated Jan. 18, 2013, for U.S. Appl. No. 13/077,813," filed Mar. 31, 2011, First Named Inventor, van der Burg. Title, Suture Passer Systems and Methods for Tongue or Other Tissue Suspension and Compression.

Synmed, "E.G. Scan: Trans-nasal, disposable system for upper GI screening," SynMed Ltd., p. 1, United Kingdom.

Mizayahi, Soichiro, M.D., et al., "A trial study of RhinoSleep for the diagnosis of sleep apnea," Psychiatry and Clinical Neuroscience, 55, pp. 249-250, 2001.

International Searching Authority, International Search Report and Written Opinion for International application no. PCT/US2014/049341, dated Nov. 19, 2014, pp. 1-11.

Bosmed, "Laryngeal and Esophageal Products," Bosmed.com, accessed Oct. 1, 2012, p. 1.

Hood Laboratories, "Schaitkin Salivary Duct Cannula," HoodLabs.com, accessed Jan. 19, 2014, pp. 1-2.

Nahlieli, Oded, et. al., "Diagnosis and treatment of strictures and kinks in salivary gland ducts," J. Oral and Maxillofacial Surgery, vol. 59, Issue 5, pp. 484-490, May 2001.

International Searching Authority, International Search Report and Written Opinion for International application No. PCT/US2014/049589, dated Dec. 3, 2014, pp. 1-16.

\* cited by examiner

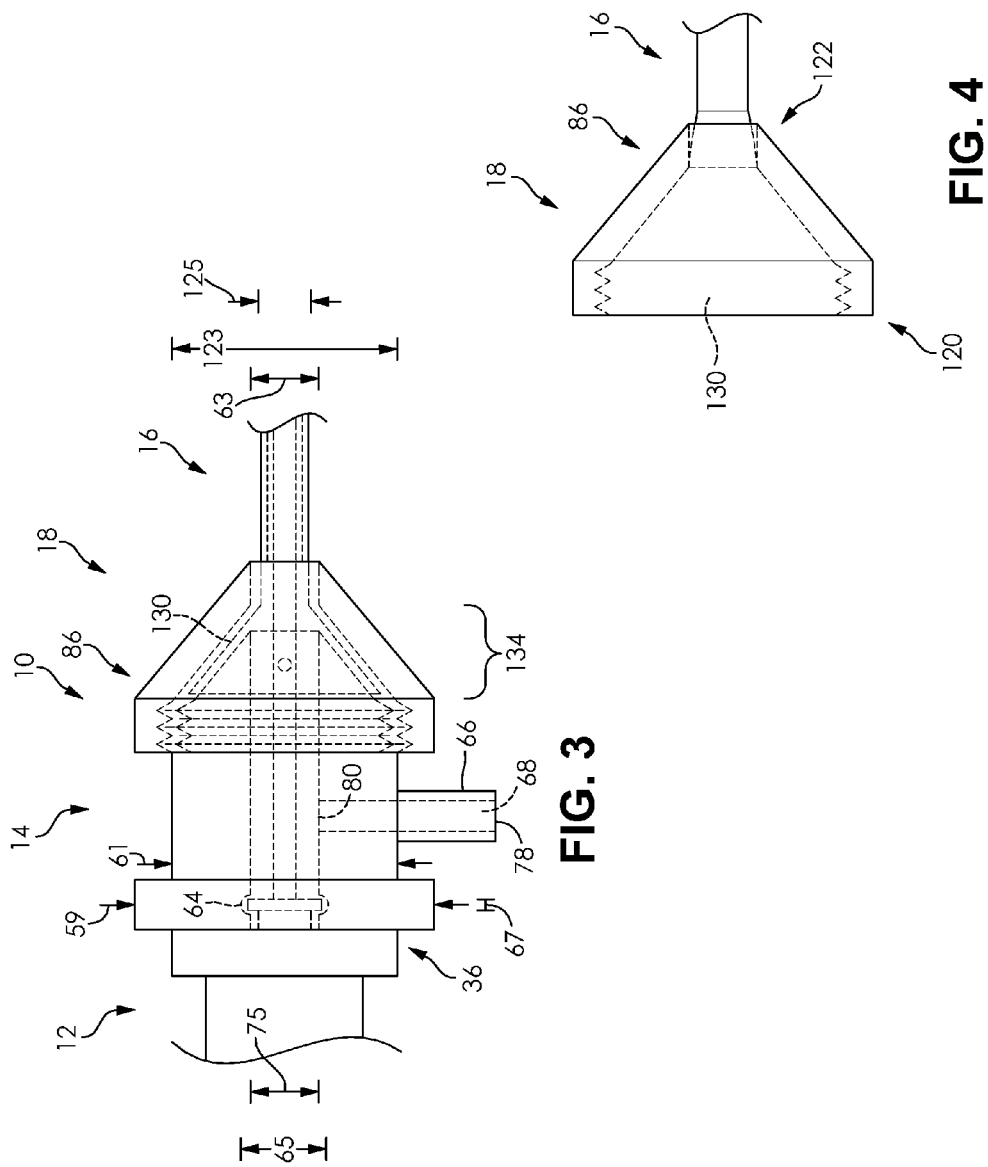

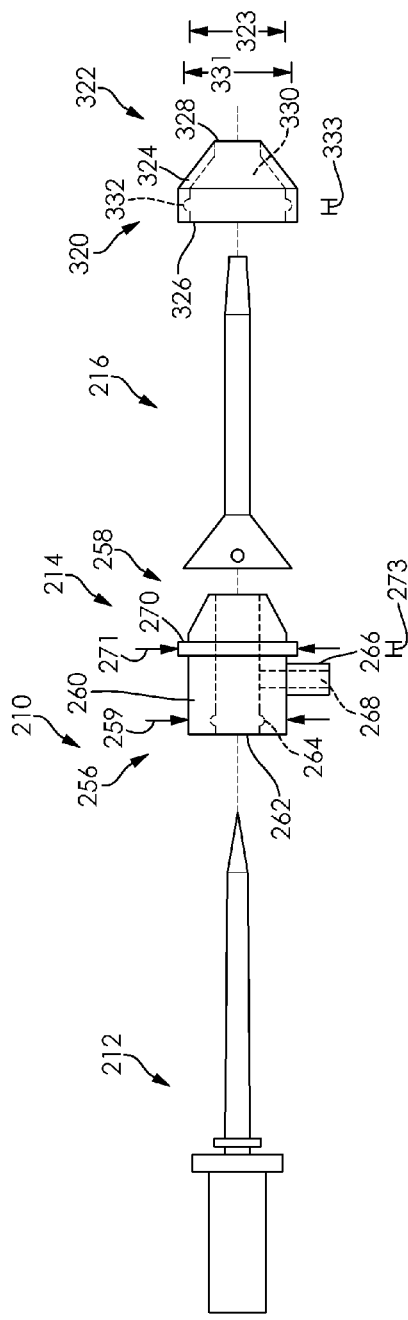

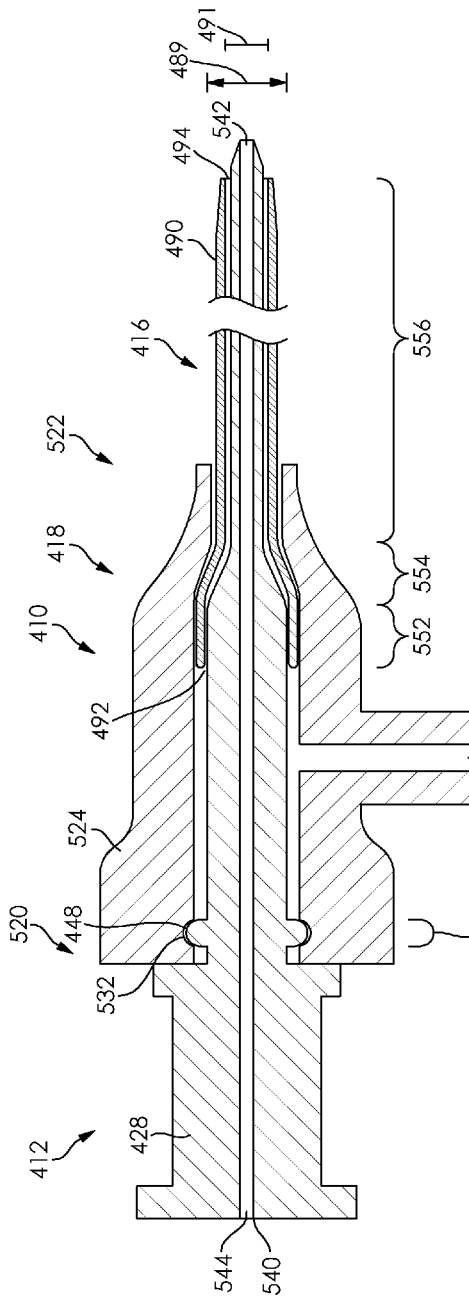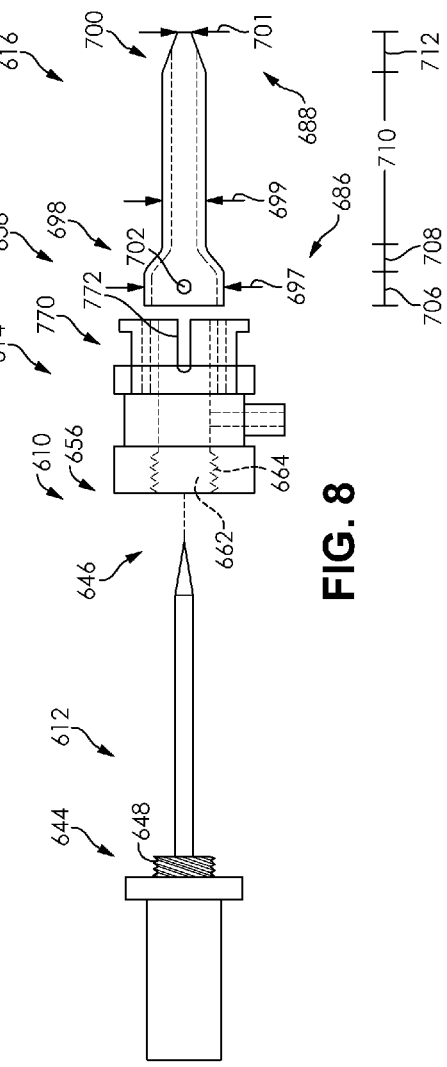

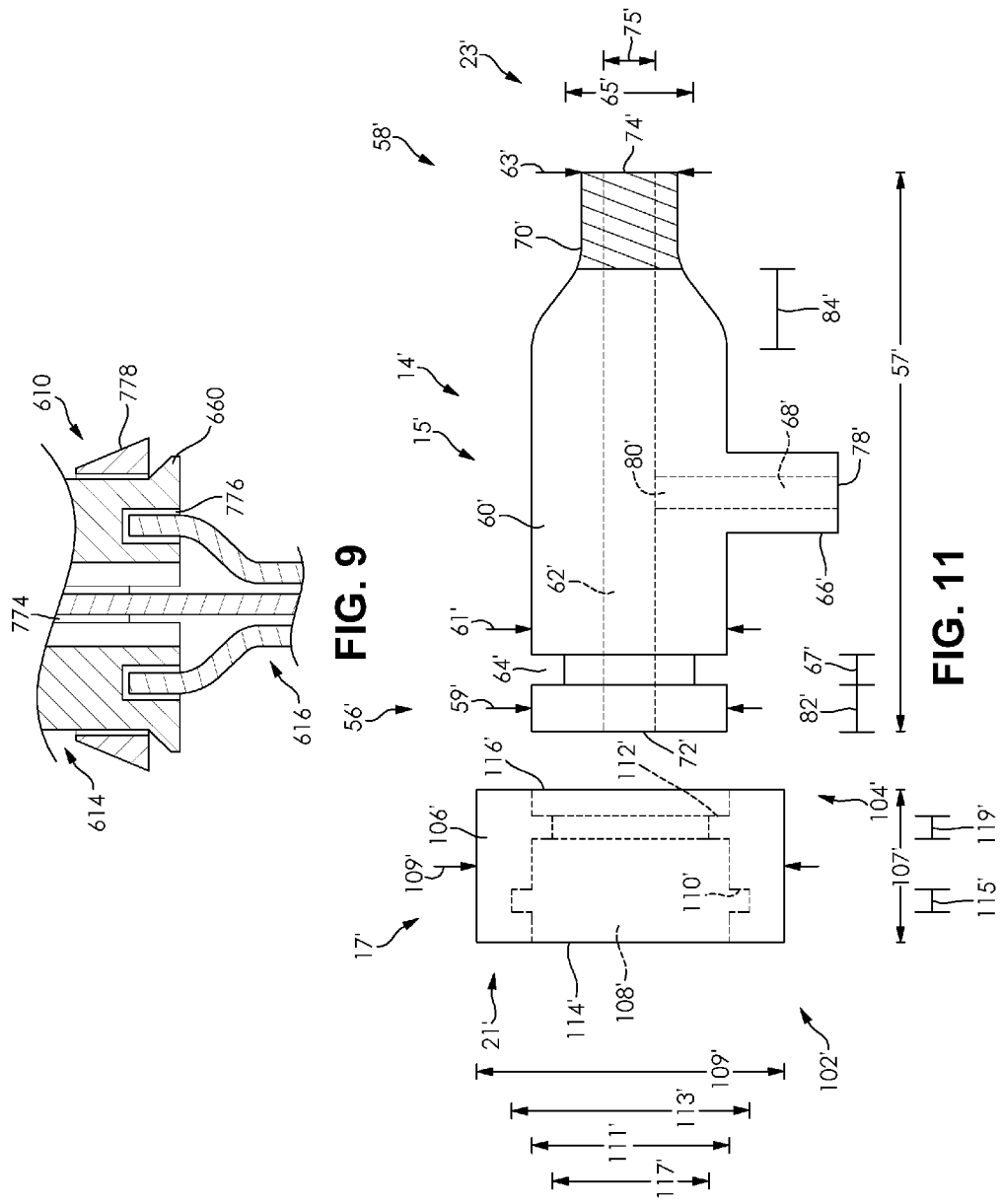

MEDICAL DEVICES HAVING A RELEASABLE MEMBER AND METHODS OF USING THE SAME

RELATED APPLICATION

This application claims the benefit of U.S. Provisional Application No. 62/003,700, filed on May 28, 2014. The disclosure of this related application is hereby incorporated into this disclosure in its entirety.

FIELD

The disclosure relates generally to the field of medical devices. Particular embodiments are related to medical devices that have a releasable member and methods of using a medical device that has a releasable member.

BACKGROUND

A variety of medical devices have been developed to treat bodily passages, such as the salivary glands. For example, some medical devices have been developed that can be introduced into a bodily passage to provide access to the bodily passage during the performance of a procedure. However, a need exists for improved medical devices that can be introduced into a bodily passage and that can be used to provide access during treatment.

BRIEF SUMMARY OF SELECTED EXAMPLE EMBODIMENTS

Medical devices are described herein. An example embodiment of a medical device comprises an elongate member, an intermediate member, a cap, and a sheath. The elongate member has a proximal portion and a shaft that extends from the proximal portion. The proximal portion has a first outside diameter. The shaft has a first proximal end attached to the proximal portion and a first distal end. The shaft has a second outside diameter that is less than the first outside diameter of the proximal portion. The intermediate member is releasably attached to the elongate member and is releasably disposed on the shaft. The intermediate member has a second proximal end, a second distal end, a third outside diameter, and an intermediate member body that defines an intermediate member lumen. The third outside diameter is greater than the first outside diameter of the proximal portion. The intermediate member lumen has a first inside diameter that is less than the first outside diameter of the proximal portion. The cap is releasably attached to the intermediate member and releasably disposed on the shaft. The cap has a third proximal end, a third distal end, and a cap body that defines a cap lumen. The sheath is partially disposed between the intermediate member and the cap and is disposed on the shaft. The sheath has a fourth proximal end, a fourth distal end, and a sheath body that defines a first sheath opening on the fourth proximal end of the sheath, a second sheath opening on the fourth distal end of the sheath, and a sheath lumen that extends from the first sheath opening to the second sheath opening. The first sheath opening has a second inside diameter that is greater than the first inside diameter of the intermediate member lumen.

Another example embodiment of a medical device comprises an elongate member, an intermediate member, a cap, and a sheath. The elongate member has a proximal portion and a shaft that extends from the proximal portion. The proximal portion has a first outside diameter. The shaft has a first proximal end attached to the proximal portion and a first distal end. The shaft has a second outside diameter that is less than the first outside diameter of the proximal portion. The intermediate member is releasably attached to the elongate member and is releasably disposed on the shaft. The intermediate member has a second proximal end, a second distal end, a third outside diameter, an outer surface, and an intermediate member body that defines an intermediate member lumen. The third outside diameter is greater than the first outside diameter of the proximal portion. The outer surface has a first tapered portion. The intermediate member lumen has a first inside diameter that is less than the first outside diameter of the proximal portion. The cap is releasably attached to the intermediate member and is releasably disposed on the shaft. The cap has a third proximal end, a third distal end, an inner surface, and a cap body that defines a cap lumen. The inner surface has a second tapered portion. The cap is formed of a first material. The sheath is disposed between and contacts the first tapered portion of the intermediate member and the second tapered portion of the cap. The sheath is disposed on the shaft and has a fourth proximal end, a fourth distal end, a tapered proximal portion, and a sheath body that defines a first sheath opening on the fourth proximal end of the sheath, a second sheath opening on the fourth distal end of the sheath, and a sheath lumen that extends from the first sheath opening to the second sheath opening. The first sheath opening has a second inside diameter that is greater than the first inside diameter of the intermediate member lumen. The sheath is formed of a second material that is relatively more flexible than the first material. The first tapered portion of the intermediate member is disposed within the sheath lumen.

Another example embodiment of a medical device comprises an elongate member, an intermediate member, a cap, and a sheath. The elongate member has a proximal portion and a shaft that extends from the proximal portion. The proximal portion has a first outside diameter. The shaft has a lengthwise axis, a first proximal end attached to the proximal portion, a first distal end, an outer surface, and a protuberance. The shaft has a second outside diameter that is less than the first outside diameter of the proximal portion. The protuberance is disposed on the outer surface of the shaft and extends away from the lengthwise axis of the shaft. The protuberance is disposed between the first proximal end and the first distal end. The intermediate member is releasably attached to the elongate member and is releasably disposed on the shaft. The intermediate member has a lengthwise axis, a second proximal end, a second distal end, a third outside diameter, an outer surface, an inner surface, and an intermediate member body that defines an intermediate member lumen, threads, and a recess. The third outside diameter is greater than the first outside diameter of the proximal portion. The outer surface has a first tapered portion. The intermediate member lumen has a first inside diameter that is less than the first outside diameter of the proximal portion. The threads of the intermediate member are defined on the outer surface of the intermediate member. The recess is defined on the inner surface and extends away from the lengthwise axis of the intermediate member. The cap is releasably attached to the intermediate member and is releasably disposed on the shaft. The cap has a third proximal end, a third distal end, an inner surface, and a cap body that defines a cap lumen and threads. The inner surface has a second tapered portion. The cap is formed of a first material. The threads of the cap are defined on the inner surface of the cap. The threads of the cap are sized and configured to mate with the threads defined by the intermediate member body. The sheath is disposed between and contacts the first tapered portion of the intermediate member and the second tapered portion of the cap. The sheath is disposed on the shaft and has a fourth proximal end, a fourth distal end, a tapered proximal portion, and a sheath body that defines a first sheath opening on the fourth proximal end of the sheath, a second sheath opening on the fourth distal end of the sheath, and a sheath lumen that extends from the first sheath opening to the second sheath opening. The first sheath opening has a second inside diameter that is greater than the first inside diameter of the intermediate member lumen. The sheath is formed of a second material that is relatively more flexible than the first material. The first tapered portion of the intermediate member is disposed within the sheath lumen. The protuberance of the shaft is disposed within the recess defined by the intermediate member.

BRIEF DESCRIPTION OF THE DRAWINGS

FIG. 3 is a magnified view of area A illustrated in FIG. 1.

FIG. 4 is a partial side view of the cap and sheath of the medical device illustrated in FIG. 1. The sheath is shown in a partially deployed configuration.

FIG. 5 is an exploded side view of another embodiment of a medical device.

FIG. 6 is an exploded side view of another embodiment of a medical device.

FIG. 7 is a sectional view of the medical device illustrated in FIG. 6.

FIG. 8 is an exploded side view of another embodiment of a medical device. The intermediate member is in a first configuration.

FIG. 9 is a partial sectional view of the medical device illustrated in FIG. 8. The intermediate member is in a second configuration.

FIG. 11 is a side view of an alternative intermediate member.

DETAILED DESCRIPTION

The following detailed description and the appended drawings describe and illustrate various example embodiments of medical devices that have a releasable member. In addition, example methods of treatment are described and illustrated. The description and illustration of these examples are provided to enable one skilled in the art to make and use a medical device and/or practice a method of treatment using a medical device. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature. The term "cuboid," or variations thereof, does not require that each side of the element or component be square and only requires that the element or component have six surfaces, hypothetical or actual, at right angles to each other. The term "bodily passage" or "body passage" refers to any passage within the body of an animal, including, but not limited to, humans, and includes elongate passages. The term "salivary duct" refers to the parotid ducts, submandibular ducts, and/or sublingual ducts. The term "urinary tract" refers to the kidneys, renal pelvis, ureters, bladder, urethra, and/or any other portion of the urinary system. The term "medication" refers to any fluid, drug, agent, therapeutic agent, and/or any other material used to treat a patient.

Figure 1:
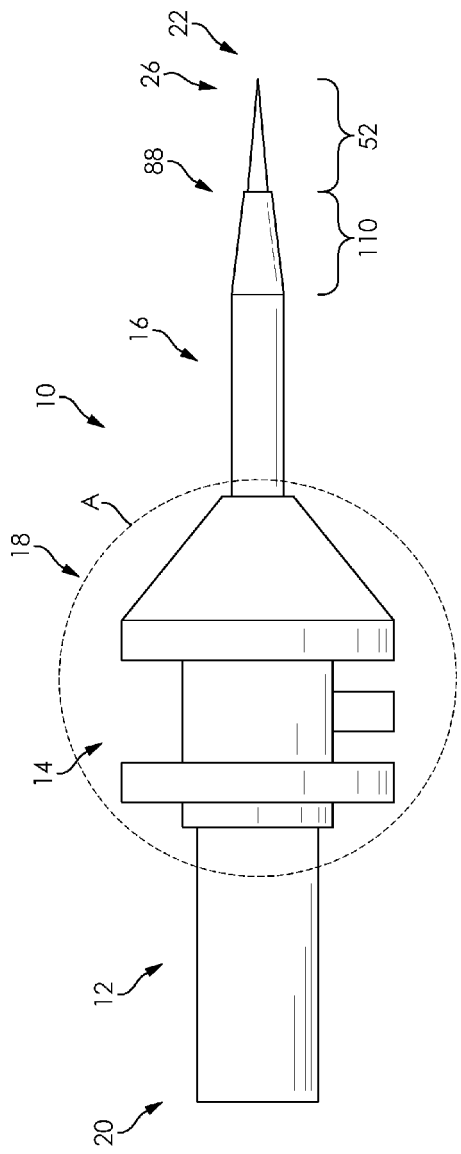
FIG. 1 is a side view of an embodiment of a medical device.
Figure 2:
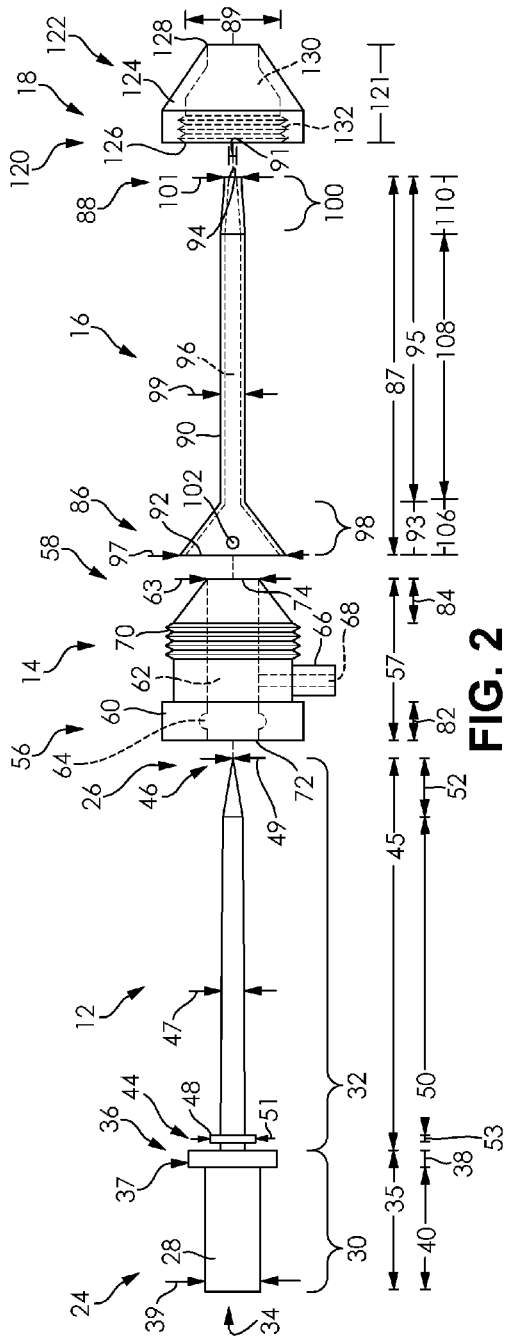
FIG. 2 is an exploded side view of the medical device illustrated in FIG. 1.

FIGS. 1, 2, 3, and 4 illustrate a medical device 10 that comprises an elongate member 12, an intermediate member 14, a sheath 16, and a cap 18. The medical device 10 has a proximal end 20 and a distal end 22. When assembled, as shown in FIG. 1, each of the intermediate member 14, sheath 16, and cap 18 is releasably disposed on the elongate member 12. In addition, when assembled, the intermediate member 14 is releasably attached to the elongate member 12, the cap 18 is releasably attached to the intermediate member 14, and the sheath 16 is releasably attached between the intermediate member 14 and the cap 18.

In the illustrated embodiment, the elongate member 12 has a proximal end 24, a distal end 26, a length 27, and a body 28 that defines a proximal portion 30 and a shaft 32. The length 27 of the elongate member 12 extends from the proximal end 24 to the distal end 26 of the elongate member 12.

The proximal portion 30 has a proximal end 34, a distal end 36, a first outside diameter 37, and a second outside diameter 39. The proximal portion has a length 35 that extends from the proximal end 34 to the distal end 36 of the proximal portion 30. The first outside diameter 37 is disposed at the distal end 36 of the proximal portion 30 and the second outside diameter 39 is disposed on the proximal end 34 of the proximal portion 30. The first outside diameter 37 is greater than the second outside diameter 39. The body 28 of the elongate member 12 defines the first outside diameter 37 along a first portion 38 of the proximal portion 30 and the second outside diameter 39 along a second portion 40 of the proximal portion 30. The first portion 38 extends from the distal end 36 toward the proximal end 34 to the second portion 40 and has a length that is less than the length 35 of the proximal portion 30. The second portion 40 extends from the first portion 38 to the proximal end 34 of the proximal portion 30 and has a length that is less than the length 35 of the proximal portion 30. The second portion 40 has a length that is greater than the length of the first portion 38.

The shaft 32 extends distally from the distal end 36 of the proximal portion 30 and has a proximal end 44, a distal end 46, and a protuberance 48. The proximal end 44 of shaft 32 is attached to the distal end 36 of the proximal portion 30. The shaft 32 has a length 45, a first outside diameter 47 and a second outside diameter 49. The length 45 of the shaft 32 extends from the proximal end 44 to the distal end 46 of the shaft 32. The first outside diameter 47 is disposed between the protuberance 48 and the distal end 46 of the shaft 32. The second outside diameter 49 is disposed at the distal end 46 of the shaft 32. The first outside diameter 47 of the shaft 32 is greater than the second outside diameter 49 of the shaft 32. The first outside diameter 47 is less than the first outside diameter 37 of the proximal portion 30.

The body 28 of the elongate member 12 defines the first outside diameter 47 along a proximal portion 50 of the shaft 32 that extends from the protuberance 48 toward the distal end 46 of the shaft 32. The first outside diameter 47 is constant along the proximal portion 50 of the shaft 32. However, alternative embodiments can include a shaft that has a first outside diameter that extends along a portion of the length of the shaft that is disposed distal to a protuberance. The first outside diameter 47 of the shaft 32 tapers to the second outside diameter 49 along a distal portion 52 of the shaft 32 that extends from the proximal portion 50 to the distal end 46 of the shaft 32. Thus, the shaft 32 has a distal portion 52 that is tapered. The proximal portion 50 has a length that is less than the length 45 of the shaft 32 and greater than the length of the distal portion 52. In the illustrated embodiment, the length 27 of the elongate member 12 is equal to the sum of the length 35 of the proximal portion 30 and the length 45 of the shaft 32. The length 35 of the proximal portion 30 is less than the length 45 of the shaft 32.

The protuberance 48 is defined between the proximal end 44 and the distal end 46 of the shaft 32. The protuberance 48 extends outward and away from the lengthwise axis of the shaft 32 and has an outside diameter 51 and a thickness 53. The outside diameter 51 of the protuberance 48 is greater than the first outside diameter 47 of the shaft 32. The thickness 53 of the protuberance 48 extends from the proximal end of the protuberance 48 to the distal end of the protuberance 48 and can be any suitable thickness capable of releasably attaching the intermediate member 14 to the elongate member 12, as described in more detail herein. The portion of the shaft 32 disposed between the proximal portion 30 and the protuberance 48 has an outside diameter that is less than the outside diameter 51 of the protuberance 48. In the illustrated embodiment, the portion of the shaft 32 disposed between the proximal portion 30 and the protuberance 48 has an outside diameter that is greater than the first outside diameter 47 of the shaft 32. However, alternative embodiments can include a portion of the shaft that is disposed between the proximal portion 30 and the protuberance 48 that has an outside diameter that is equal to, substantially equal to, or less than the first outside diameter 47 of the shaft 32. While the protuberance 48 is described as defined by the body 28 of the elongate member 12, a protuberance can alternatively be a separate component attached to the shaft of an elongate member using any suitable technique or method of attachment, such as welding, or by using adhesives.

While the elongate member 12 has been illustrated as having a particular structural arrangement, an elongate member can have any suitable structural arrangement. Skilled artisans will be able to select a suitable structural arrangement for an elongate member according to a particular embodiment based on various considerations, including the structural arrangement of an intermediate member, a sheath, and/or cap included in a medical device of which the elongate member is a component. Example structural arrangements considered suitable for the proximal portion of an elongate member include a proximal portion that has an outside diameter that is constant, or substantially constant, along a portion, or the entirety, of its length, a proximal portion that has an outside diameter along a portion, or the entirety, of its length that is equal to, or substantially equal to, the first outside diameter, or any outside diameter, of a shaft, a proximal portion that has an outside diameter that is equal to, or substantially equal to, the first outside diameter of a shaft and that defines one or more protuberances that extend outward and away from the lengthwise axis of the elongate member (e.g., each protuberance providing a mechanical stop to proximal advancement of an intermediate portion and/or sheath along the elongate member), and any other structural arrangement considered suitable for a particular application. Example structural arrangements considered suitable for the shaft of an elongate member include a shaft that has a constant, or substantially constant, outside diameter along a portion, or the entirety, of its length, a shaft that omits the inclusion of a tapered distal portion, a shaft that has a diameter that varies along a portion, or the entirety, of its length, and any other structural arrangement considered suitable for a particular application. Optionally, an elongate member can define a lumen that extends through the proximal portion and the shaft. The lumen can be sized and configured to receive any suitable medical device, such as a guide wire.

The shaft 32 can be attached to the distal end 36 of proximal portion 30 using any suitable technique or method of attachment. Skilled artisans will be able to select a suitable technique or method of attachment between the shaft and the proximal portion of an elongate member according to a particular embodiment based on various considerations, including the material(s) that forms the proximal portion and/or the shaft. Examples of suitable techniques and methods of attachment considered suitable between the proximal portion and the shaft of an elongate member include using an adhesive, welding, fusing (e.g., heat fusing), threaded connections, integrated components, insert molding, and any other technique or method of attachment considered suitable for a particular application. For example, the shaft 32 can be fabricated and subsequently the proximal portion 30 and/or protuberance 48 can be molded onto, or attached to, the shaft 32.

The elongate member 12 can be formed of any suitable material. Skilled artisans will be able to select a suitable material to form an elongate member according to a particular embodiment based on various considerations, including the material(s) that forms an intermediate member, a sheath, and/or a cap included in a medical device of which the elongate member is a component. Example materials considered suitable to form an elongate member include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, silicone, acrylonitrile butadiene styrene (ABS), polyoxymethylene (e.g., acetal), and any other material considered suitable for a particular application. In the illustrated embodiment, the elongate member 12 is formed of high-density polyethylene (HDPE).

In the illustrated embodiment, the intermediate member 14 comprises a proximal end 56, a distal end 58, and a body 60. The intermediate member 14 has a length 57, a first outside diameter 59, a second outside diameter 61, and a third outside diameter 63. The length 57 extends from the proximal end 56 to the distal end 58 of the intermediate member 14. The body 60 of the intermediate member 14 defines a first lumen 62, a recess 64, a port 66, a second lumen 68, and threads 70.

The first lumen 62 extends from a first opening 72 defined on the proximal end 56 of the intermediate member 14 to a second opening 74 defined on the distal end 58 of the intermediate member 14. Each of the first lumen 62, first opening 72, and second opening 74 has an inside diameter that is sized and configured to receive the shaft 32. In the illustrated embodiment, each of the first lumen 62, first opening 72, and second opening 74 has an inside diameter 75 that is less than the first outside diameter 37 of the proximal portion 30 and greater than the first outside diameter 47 of the shaft 32. However, other inside diameters are considered suitable for each of the first lumen, first opening, and second opening, such as inside diameters that are less than, equal to, substantially equal to, or greater than the diameters of other features described herein (e.g., outside diameter of shaft 32).

The recess 64 is defined between the proximal end 56 and the distal end 58 of the intermediate member 14 within the first lumen 62 and has an inside diameter 65 and a length 67. The recess 64 extends from the inner surface of the intermediate member 14 and away from the lengthwise axis of the intermediate member 14. The inside diameter 65 is greater than the inside diameter 75 of the first lumen 62. The recess 64 is sized and configured to receive the protuberance 48 defined by the elongate member 12. The inside diameter 65 of the recess 62 is equal to the outside diameter 51 of the protuberance 48 and the length 67 of the recess 64 is equal to the thickness 53 of the protuberance 48. This configuration provides a mechanism to releasably attach the intermediate member 14 to the elongate member 12 using a snap fit connection between the intermediate member 14 and the elongate member 12. However, alternative embodiments can include a recess that has an inside diameter that is greater than, substantially equal to, or less than the outside diameter of a protuberance and/or a recess that has a length that is greater than, substantially equal to, or less than the thickness of the protuberance. Alternatively, an elongate member can define a recess and an intermediate member can define a protuberance.

The port 66 is disposed between the proximal end 56 of the intermediate member 14 and the threads 70. The second lumen 68 extends from a third opening 78 defined on the port 66 to a fourth opening 80 defined between the proximal end 56 and the distal end 58 of the intermediate member 14. The fourth opening 80 is in fluid communication with the first lumen 62. Thus, the second lumen 68 is in fluid communication with the first lumen 62. Port 66 provides a mechanism for providing treatment via the second lumen 68, such as by applying suction to the second lumen 68 using a suction device attached to the port 66 or that is in communication with the second lumen 68.

The port 66 can include any suitable connector and/or adapter capable of attaching one or more devices to the intermediate member 14. Skilled artisans will be able to select a suitable connector and/or adapter to include on a port of an intermediate member according to a particular embodiment based on various considerations, including the material(s) that forms the intermediate member. Example connectors and/or adapters considered suitable to include on a port of an intermediate member include threaded connectors, Tuohy Borst adapters, luer lock connectors, and any other connector and/or adapter considered suitable for a particular embodiment.

Threads 70 are disposed between the port 66 and the distal end 58 of the intermediate member 14 and have a helical configuration that is sized and configured to interact with the helical configuration defined by threads 132 defined by the cap 18, as described herein. For example, as shown in FIG. 3, the threads 70 defined by the intermediate member 14 are sized and configured to mate with the threads 132 defined by the cap 18 such that the cap 18 is releasably attached to the intermediate member 14 using threads 70 and threads 132. Threads 70 provide a mechanism to releasably attach the cap 18 to the intermediate member 14. Alternative embodiments can include threads that extend from the distal end of the intermediate member toward the proximal end of the intermediate member.

The intermediate member 14 has a first outside diameter 59, a second outside diameter 61, and a third outside diameter 63. The first outside diameter 59 is greater than the first outside diameter 37 of the proximal portion 30. The first outside diameter 59 extends along a proximal portion 82 of the intermediate member 14 that extends from the proximal end 56 toward the distal end 58. The second outside diameter 61 is less than the first outside diameter 59 and extends from the proximal portion 82 of the intermediate member 14 toward the distal end 58 of the intermediate member 14. The third outside diameter 63 is disposed on the distal end 58 of the intermediate member 14 and is less than the second outside diameter 61. The intermediate member 14 has an outer surface that defines a tapered portion 84 that extends from threads 70 toward the distal end 58 of the intermediate member 14. However, alternative embodiments can include a tapered portion that extends from a location proximal or distal to the threads and toward the distal end or to the distal end. The tapered portion 84 tapers from the second outside diameter 61 to the third outside diameter 63. The tapered portion 84 is sized and configured such that a portion of the tapered portion 84 can be received by the sheath 16, as described in more detail herein.

The intermediate member 14 can be formed of any suitable material. Skilled artisans will be able to select a suitable material to form an intermediate member according to a particular embodiment based on various considerations, including the material(s) that forms an elongate member, sheath, and/or cap included in a medical device of which the intermediate member is a component. Example materials considered suitable to form an intermediate member include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular application. In the illustrated embodiment, the intermediate member is formed of high-density polyethylene (HDPE). Optionally, an intermediate member can be formed of a material that is relatively more flexible than, or relatively more rigid than, a material that forms an elongate member, sheath, and/or a cap (e.g., intermediate member is formed of a material that has a higher durometer hardness than the material that forms the elongate member, sheath, and/or cap).

In the embodiment illustrated, the protuberance 48 defined by the elongate member 12 is formed of the same material that forms the intermediate member 14 and the geometry of the protuberance 48 (e.g., outside diameter 51 and/or thickness 53) is configured such that a portion of the protuberance 48 can collapse, or compress, on itself as it is passed through the first opening 72 defined by the intermediate member 14 and into the recess 64. However, alternative embodiments can include a protuberance that is formed of the same material as, or a material that is different than, the elongate member and/or a material that is different than the material that forms the intermediate member. The material that forms the protuberance 48 can expand, or return to its original structural configuration, or a configuration that is substantially similar to its original structural configuration, when it is disposed within recess 64 or removed from the intermediate member 14. Alternatively, the protuberance defined by an elongate member can be formed of a material that is relatively more flexible than the material that forms an intermediate member (e.g., proximal end of an intermediate member) such that the protuberance can collapse, or compress, on itself as it is passed through the first opening defined by the intermediate member and into the recess. In addition, the material that forms the protuberance can expand, or return to its original structural configuration, or a configuration that is substantially similar to its original structural configuration, when it is disposed within recess or removed from the intermediate member. For example, the material that forms the protuberance of an elongate member, or a portion of the protuberance, can have a first durometer hardness and the material that forms an intermediate member, or a portion of an intermediate member, can have a second durometer hardness that is greater than the first durometer hardness. Alternatively, a portion (e.g., proximal end, portion that forms the first lumen), or the entirety, of an intermediate member can be formed of a material that is relatively more flexible than the material that forms the protuberance defined by an elongate member such that the intermediate member can expand and allow the protuberance to be passed through the first opening and first lumen defined by the intermediate member until the protuberance is disposed within the recess defined by the intermediate member. For example, a portion (e.g., proximal end, portion that forms the first lumen), or the entirety, of an intermediate member can be formed of a material that has a first durometer hardness and the material that forms the protuberance defined by an elongate member can have a second durometer hardness that is greater than the first durometer hardness such that the intermediate member can expand and allow the protuberance to be passed through the first opening and first lumen until the protuberance is disposed within the recess defined by the intermediate member.

While an interlocking structure has been illustrated between the elongate member 12 and the intermediate member 14, any suitable locking structure can be included on an elongate member and/or an intermediate member to provide releasable attachment between the elongate member and the intermediate member. Skilled artisans will be able to select a suitable locking structure to include on an elongate member and/or intermediate member according to a particular embodiment based on various considerations, including the material(s) that forms the elongate member and the intermediate member. Example locking structures considered suitable between an elongate member and an intermediate member include interlocking structures, structures that provide a friction fit between the elongate member and the intermediate member, morse taper configurations, threaded connections, mechanical fasteners, and any other structure considered suitable for a particular embodiment.

In use, the shaft 32 of the elongate member 12 is passed through the first lumen 62 such that the protuberance 48 is partially disposed within the recess 64. Depending on the structural configuration of the recess defined by an intermediate member, alternative embodiments can include a protuberance that is entirely disposed within a recess defined by an intermediate member when the two components are releasably attached to one another.

While the intermediate member 14 has been illustrated as having a particular structural arrangement, an intermediate member can have any suitable structural arrangement. Skilled artisans will be able to select a suitable structural arrangement for an intermediate member according to a particular embodiment based on various considerations, including the structural arrangement of an elongate member, sheath, and/or cap included in a medical device of which the intermediate member is a component. Example structural arrangements considered suitable for an intermediate member include intermediate members that omit the inclusion of a port, intermediate members that omit the inclusion of a recess, and any other structural arrangement considered suitable for a particular application.

While each of the first lumen 62, first opening 72, and second opening 74 has been illustrated as having an inside diameter 75 that is greater than the first outside diameter 47 of the shaft 32, the first lumen, first opening, and/or second opening of an intermediate member can have any suitable diameter, such as a diameter that is greater than, equal to, substantially equal to, or less than the first outside diameter of a shaft. For example, when an intermediate member is formed of a material that is relatively more flexible than a material that forms an elongate member, a first lumen, first opening, and/or second opening can have a diameter that is equal to, substantially equal to, or less than the first outside diameter of a shaft. In these embodiments, the first opening, second opening, and/or lumen can expand when the shaft is passed through, or disposed within, the first opening, second opening, and/or lumen to provide a friction fit between the two components.

In the illustrated embodiment, the sheath 16 is releasably disposed on the shaft 32 between the intermediate member 14 and the cap 18. The sheath 16 is separable from the intermediate member 14 and comprises a proximal end 86, a distal end 88, and a body 90. The sheath has a length 87 that extends from the proximal end 86 to the distal end 88 and is less than the length 45 of shaft 32. The body 90 of the sheath 16 defines a first opening 92, a second opening 94, a lumen 96, a flared proximal portion 98, a tapered distal portion 100, and a passageway 102. The first opening 92 is defined on the proximal end 86 and the second opening 94 is defined on the distal end 88. The lumen 96 extends from the first opening 92 to the second opening 94.

The first opening 92 has a first inside diameter 89 and the second opening 94 has a second inside diameter 91. Thus, the lumen 96 has a first inside diameter 89 and a second inside diameter 91. The first inside diameter 89 is greater than the second inside diameter 91 and is greater than the first outside diameter 47 of the shaft 32. The second inside diameter 91 is greater than the first outside diameter 47 of the shaft 32. Alternatively, the second inside diameter of a sheath can be equal to, substantially equal to, or less than the first outside diameter of a shaft such that a friction fit between the sheath and shaft can be accomplished. The first inside diameter 89 tapers to the second inside diameter 91 along a proximal portion 93 of the lumen 96 that extends from the proximal end 86 toward the distal end 88 to a location between the proximal end 86 and the distal end 88. The second inside diameter 91 extends along a distal portion 95 of the lumen 96 that extends from the proximal portion 93 to the distal end 88 of the sheath 16. The proximal portion 93 of the lumen 96 has a structural arrangement that is complementary to the structural arrangement of the tapered portion 84 defined by the intermediate member 14. The proximal portion 93 of the lumen 96 is sized and configured to receive the tapered portion 84 such that a portion of the intermediate member 14 is disposed within the sheath 16 when the medical device 10 is assembled. Alternatively, the proximal portion of the lumen of a sheath can be sized and configured to receive a portion of a tapered portion defined by an intermediate member such that a portion of the intermediate member is disposed within the sheath. The proximal portion 93 of lumen 96 is frustoconical and tapers from the proximal end 86 of the sheath 16 toward the distal end 88.

The sheath 16 has a first outside diameter 97, a second outside diameter 99, and a third outside diameter 101. The first outside diameter 97 is disposed on the proximal end 86, the second outside diameter 99 is disposed between the proximal end 86 and the distal end 88, and the third outside diameter 101 is disposed on the distal end 88. The first outside diameter 97 is greater than the second outside diameter 99 and the second outside diameter 99 is greater than the third outside diameter 101. The first outside diameter 97 tapers to the second outside diameter 99 along a proximal portion 106 of the sheath 16 that extends from the proximal end 86 toward the distal end 88 and defines the flared proximal portion 98. The flared proximal portion 98 acts as a mechanical stop to distal advancement of the sheath 16 beyond tissue disposed outside of a bodily passage (e.g., the flared proximal portion contacts tissue disposed outside of a bodily passage). The flared proximal portion 98 is frustoconical and tapers from the proximal end 86 of the sheath 16 toward the distal end 88. The second outside diameter 99 extends along an intermediate portion 108 of the sheath 16 that extends from the proximal portion 106 toward the distal end 88. The second outside diameter 99 tapers to the third outside diameter 101 along a distal portion 110 of the sheath 16 and defines the tapered distal portion 100.

The passageway 102 is disposed on the flared proximal portion 98 of sheath 16 between the proximal end 86 and the distal end 88 of the sheath 16. The passageway 102 extends through the body 90 of the sheath 16 and provides access to lumen 96. The passageway 102 has a diameter that is sized and configured to receive a suture, or one or more lengths of a suture. The passageway 102 can have any suitable structural arrangement. For example, a passageway can have a structural arrangement that defines any suitable geometric shape, such as a cylinder, cuboid, cube, triangular prism, sphere, semi-sphere, and any other structural arrangement considered suitable for a particular embodiment. In the illustrated embodiment, the passageway 102 is cylindrical.

While the sheath 16 has been illustrated as having a particular structural arrangement, a sheath can have any suitable structural arrangement. Skilled artisans will be able to select a suitable structural arrangement for a sheath according to a particular embodiment based on various considerations, including the structural arrangement of an elongate member, intermediate member, and/or cap included in a medical device of which the sheath is a component. Example structural arrangements considered suitable for a sheath include sheaths that omit the inclusion of a flared proximal portion, sheath that omit the inclusion of a tapered distal end, sheaths that omit the inclusion of a flared proximal portion and a tapered distal end, sheaths that define a barrel flared proximal portion alternative to a flared proximal portion, sheaths in which a lumen defined by the sheath has a constant, or substantially constant, inside diameter along a portion, or the entirety, of its length, and any other structural arrangement considered suitable for a particular application. For example, a sheath, such as those described herein, can include a completely circumferentially closed member, a member that defines a slit along the entirety, or a portion, of its length, a member that defines one or more, or a plurality, of perforations along its length, a tubular member, and any other structural configuration considered suitable for a particular embodiment.

While the body 90 of the sheath 16 has been illustrated as defining a passageway 102 that extends through the body 90 of the sheath 16 on the flared proximal portion 98 of the sheath 16, the body of a sheath can define any suitable number of passageways and each passageway can extend through any suitable portion of a sheath. Skilled artisans will be able to select a suitable number of passageways to define on a sheath and a suitable location to position each passageway according to a particular embodiment based on various considerations, including the structural arrangement of a bodily passage within which a sheath is intended to be disposed. Example number of passageways considered suitable to include on a sheath include one, at least one, two, a plurality, three, four, five, six, seven, and any other number considered suitable for a particular application. Example locations considered suitable to define a passageway on a sheath include on the flared proximal portion of a sheath, between the proximal end and the distal end of a sheath, on the tapered distal portion of a sheath, and any other location considered suitable for a particular application. A passageway defined by a sheath can have any suitable diameter, such as a diameter that is greater than, equal to, substantially equal to, or less than the outside diameter of a suture, one or more sutures, or a plurality of sutures.

The sheath 16 can be formed of any suitable material. Skilled artisans will be able to select a suitable material to form a sheath according to a particular embodiment based on various considerations, including the material(s) that forms an elongate member, an intermediate member, and/or a cap included in a medical device of which the sheath is a component. Example materials considered suitable to form a sheath include biocompatible materials, materials that can be made biocompatible, biodegradable materials, bioabsorbable materials such as chitosan, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polytetrafluoroethylene (PTFE), silicone, acrylonitrile butadiene styrene (ABS), polyoxymethylene (e.g., acetal), and any other material considered suitable for a particular application.

In embodiments in which the sheath 16 is formed of a bioabsorbable material, such as chitosan, the material can be formed such that it has a first stiffness when the material is in a dehydrated, or substantially dehydrated, state and a second stiffness when the material is in a hydrated, or substantially hydrated, state. The second stiffness being relatively more flexible than the first stiffness. In use, a sheath that has been formed of a material having these properties, such as chitosan, can be provided in a dehydrated state and hydrated prior to being positioned on a shaft, prior to being inserted into a bodily passage, or can be inserted into a bodily passage in a dehydrated state and allowed to hydrate inside the bodily passage.

In the embodiment illustrated, the sheath 16 is formed of a material that is relatively more flexible than the material that forms the cap 18 such that the sheath 16 can collapse, or compress, on itself as it is passed through the lumen 130 defined by the cap 18, as described in more detail herein.

Once the sheath 16 is free of the cap 18, the sheath 16 can expand, or return to its original structural configuration, or a configuration that is substantially similar to its original structural configuration. For example, the material that forms the sheath 16, or a portion of the sheath 16 (e.g., flared proximal portion 98), can have a first durometer hardness and the material that forms the cap 18, or a portion of the cap 18 (e.g., distal end 122), can have a second durometer hardness that is greater than the first durometer hardness. Alternatively, a portion (e.g., distal end, portion that forms the lumen of the cap), or the entirety, of the cap can be formed of a material that is relatively more flexible than the material that forms the sheath such that the cap can expand and allow the sheath to be passed through the lumen defined by the cap until the sheath is free of the cap. For example, a portion (e.g., distal end, portion that forms the lumen of the cap), or the entirety, of the cap can be formed of a material that has a first durometer hardness and the material that forms the sheath can have a second durometer hardness that is greater than the first durometer hardness such that the cap can expand and allow the sheath to be passed through the lumen defined by the cap until the sheath is free of the cap. Alternatively, a sheath can be formed of the same material that forms a cap and the geometry of the sheath (e.g., thickness of sheath) is configured such that a portion of the sheath can collapse, or compress, on itself as it is passed through the second opening defined by the cap. The material that forms the sheath can expand, or return to its original structural configuration, or a configuration that is substantially similar to its original structural configuration, when it is free of the cap.

Optionally, a sheath can have a first portion that is relatively more flexible than a second portion when the sheath is free of the elongate member, intermediate member, and/or cap included in a medical device of which the sheath is a component. Thus, the second portion can be relatively more rigid than the first portion. The first portion can extend from the proximal end toward the distal end to a location disposed between the proximal end and the distal end. The second portion can extend from the distal end to a location disposed between the proximal end and the distal end. The first portion can be formed of a first material and the second portion can be formed of a second material. The first material can be the same as, or different than, the second material. For example, the first portion can be formed of a material that has a first durometer hardness and the second portion can be formed of a material that has a second durometer hardness. The first durometer hardness is less than the second durometer hardness. For example, a sheath can have a proximal end, or a proximal portion that extends from the proximal end toward the distal end, that has a first durometer hardness that is less than a second durometer hardness at the distal end, or along a distal portion that extends from the distal end toward the proximal end. Optionally, the material of a sheath can define a flared proximal portion that has a first durometer hardness that is less than a second durometer hardness along a portion of the sheath that extends from the flared proximal portion to the distal end of the sheath, or a location between the flared proximal portion and the distal end of the sheath. Alternatively, the first portion can be relatively more rigid than the second portion.

In embodiments in which the first portion is formed of a first material that is different than a second material that forms the second portion, the first portion and the second portion can be attached to one another using any suitable technique or method of attachment. Examples of suitable techniques and methods of attachment considered suitable to attach a first portion and a second portion of a sheath include using an adhesive, welding, fusing (e.g., heat fusing), threaded connections, and any other technique or method of attachment considered suitable for a particular application.

In the illustrated embodiment, the cap 18 is releasably attached to the intermediate member 14 and is releasably disposed on the shaft 32. The cap 18 comprises a proximal end 120, a distal end 122, and a body 124. The cap 18 has a length 121 that extends from the proximal end 120 to the distal end 122. The body 124 of the cap 18 defines a first opening 126, a second opening 128, a lumen 130, and threads 132. The first opening 126 is defined on the proximal end 120 and the second opening 128 is defined on the distal end 122. The lumen 130 extends from the first opening 126 to the second opening 128.

The lumen 130 has a first inside diameter 123 and a second inside diameter 125. The first inside diameter 123 is disposed along a proximal portion of the lumen 130 that extends from the proximal end 120 of the cap 18 toward the distal end 122 of the cap 18. The second inside diameter 125 is less than the first inside diameter 123 and is disposed along a distal portion of the lumen 130 that extends from the distal end 122 toward the proximal end 120. The first inside diameter 123 tapers to the second inside diameter 125 along a tapered portion 134 of the inner surface of the cap 18 defined between the proximal portion and the distal portion of the cap 18. Thus, the tapered portion 134 of the cap 18 is disposed between the proximal end 120 and the distal end 122 of the cap 18. In the illustrated embodiment, the tapered portion 134 of the lumen 130 corresponds to the taper defined by the flared proximal portion 98 of the sheath 16. However, alternative embodiments can include a cap that has a first inside diameter that tapers to a second inside diameter along a portion, or the entirety, of the length of the cap (e.g., along a proximal portion of the cap that extends from the proximal end toward the distal end, along a distal portion of the cap that extends from the distal end toward the proximal end).

Threads 132 are disposed between the proximal end 120 and the distal end 122 of the cap 18 within lumen 130 and have a helical configuration that is sized and configured to interact with the helical configuration defined by threads 70 defined by the intermediate member 14. For example, as shown in FIG. 3, the threads 132 defined by the cap 18 are sized and configured to mate with the threads 70 defined by the intermediate member 14 such that the cap 18 is releasably attached to the intermediate member 14 using threads 70 and threads 132. Threads 132 provide a mechanism to releasably attach the cap 18 to the intermediate member 14.

While an interlocking structure has been illustrated between the intermediate member 14 and the cap 18, any suitable locking structure can be included on an intermediate member and/or a cap to provide releasable attachment between the intermediate member and the cap. Skilled artisans will be able to select a suitable locking structure to include on an intermediate member and/or cap according to a particular embodiment based on various considerations, including the material(s) that forms the intermediate member and the cap. Example locking structures considered suitable include interlocking structures, structures that provide a friction fit between the intermediate member and the cap, morse taper configurations, threaded connections, mechanical fasteners, and any other structure considered suitable for a particular embodiment.

The cap 18 can be formed of any suitable material. Skilled artisans will be able to select a suitable material to form a cap according to a particular embodiment based on various considerations, including the material(s) that forms an elongate member, an intermediate member, and/or a sheath included in a medical device of which the cap is a component. Example materials considered suitable to form a cap include biocompatible materials, materials that can be made biocompatible, biodegradable materials, bioabsorbable materials such as chitosan, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polytetrafluoroethylene (PTFE), silicone, acrylonitrile butadiene styrene (ABS), polyoxymethylene (e.g., acetal), and any other material considered suitable for a particular application. In the illustrated embodiment, the cap is formed of acetal.

In use, the distal end 58 of the intermediate member 14 is positioned within the proximal portion 93 of lumen 96 of the sheath 16 and is passed through the first opening 126 of the cap 18 and into the lumen 130 defined by the cap 18 until threads 70 contact threads 132. Subsequently, a rotational force can be applied to one, or both, of the intermediate member 14 or the cap 18 such that the threads 70, 132 interlock with one another. When the medical device 10 is fully assembled, as illustrated in FIG. 1, the distal end 88 of the sheath 16 is disposed proximal to the distal end 26 of the elongate member 12. In the illustrated embodiment, the distal portion 52 of the shaft 32 is disposed distal to the distal end 88 of the sheath 16. In addition, the distal portion 110 of sheath 16 is disposed proximal to the distal portion 52 of the shaft 32. This structural arrangement provides an assembled medical device 10 that has a tapered distal end and provides a mechanism for reducing the trauma to a bodily passage as the medical device 10 is advanced into the bodily passage. Alternatively, a portion of the distal portion of a shaft can be disposed distal to the distal end of a sheath and/or a portion of the distal portion of a sheath can be disposed proximal to the second portion of a shaft.

When the medical device 10 is fully assembled, the intermediate member 14 is releasably attached to the shaft 32 between the distal end 36 of the proximal portion 30 and the proximal end 86 of the sheath 16. Thus, the intermediate member 14 is disposed between the proximal portion 30 and the sheath 16. The sheath 16 is releasably disposed on the shaft 32 and is disposed distal to the intermediate member 14 such that a portion of the intermediate member 14 (e.g., tapered portion 84) is disposed within the lumen 96 defined by the sheath 16 (e.g., within the proximal portion 93 of the lumen 96).

When assembled, the sheath 16 is disposed between the intermediate member 14 and the cap 18 and is releasably attached to the intermediate member 14 and the cap 18. When the intermediate member 14 and the cap 18 are releasably attached to one another (e.g., via threads 70 and threads 132), the outer surface of the intermediate member 14 (e.g., tapered portion 84) contacts the inner wall of the sheath 16 (e.g., proximal portion 93) and the outer surface of the sheath 16 (e.g., flared proximal portion 98) contacts the inner surface of the cap 18 (e.g., tapered portion 134) such that the sheath 16 is compressed, or pinched, between the intermediate member 14 and the cap 18, as shown in FIG. 3. This provides a mechanism for advancing the sheath 16 into a bodily passage and for providing suction, or other treatment, through the port 66 after the elongate member 12 has been removed from the medical device 10.

In the illustrated embodiment, the first outside diameter 59 of the intermediate member 14 is greater than the first outside diameter 37 of the proximal portion 30. This structural arrangement provides a pushing surface (e.g., the length of the intermediate member 14 that extends beyond the first outside diameter 37 of the proximal portion 30) that can be used to remove the intermediate member 14, the sheath 16, and the cap 18 from the elongate member 12 during use. For example, after a portion of the medical device 10 (e.g., portion of shaft, portion of sheath) has been introduced into a bodily passage, salivary duct, or a portion of the urinary tract, a distally-directed force can be applied on the intermediate member 14 (e.g., the length of the intermediate member 14 that extends beyond the first outside diameter 37 of the proximal portion) to advance the intermediate member 14, the sheath 16, and the cap 18 distally along the shaft 32 until each of the intermediate member 14, the sheath 16, and the cap 18 become free of the elongate member 12. Alternatively, after a portion of the medical device 10 (e.g., portion of shaft, portion of sheath) has been introduced into a bodily passage, the position of the intermediate member 14 can be maintained, and/or a distally-directed force can be applied to the intermediate member 14, relative to the tissue disposed outside of the bodily passage and/or the bodily passage while a proximally-directed force is applied on the elongate member 12 (e.g., proximal portion 30) to advance the elongate member 12 proximally until it becomes free of the intermediate member 14, the sheath 16, and the cap 18. Subsequently, the intermediate member 14 can be separated from the cap 18 and the cap 18 can be pulled over the proximal end 86 of the sheath 16, as illustrated in FIG. 4. The sheath 16 can be used to complete treatment on, or within, the bodily passage and can be left in the bodily passage for an interval of time, or removed subsequent to the treatment being performed. Optionally, the sheath 16 can be sutured to the tissue disposed outside of the bodily passage and/or the bodily passage wall. This can be accomplished, for example, using passageway 102.

Each of the elongate member 12, intermediate member 14, sheath 16, and cap 18 can be fabricated using any suitable technique or method of manufacture. Skilled artisans will be able to select a suitable technique or method of manufacture to fabricate an elongate member, intermediate member, sheath, and/or cap according to a particular embodiment based on various considerations, including the material(s) that forms each component. Example techniques and methods of manufacture considered suitable to fabricate an elongate member, intermediate member, sheath, and/or a cap include extrusion processes, molding processes, insert molding, and any other technique or method considered suitable for a particular application.

FIG. 5 illustrates another medical device 210. The medical device 210 is similar to the medical device 10 illustrated in FIGS. 1, 2, 3, and 4 and described above, except as detailed below. Reference numbers in FIG. 5 refer to the same structural element or feature referenced by the same number in FIGS. 1, 2, 3, and 4, offset by 200. Thus, the medical device 210 comprises an elongate member 212, an intermediate member 214, a sheath 216, and a cap 218.

In this embodiment, the body 260 of the intermediate member 214 defines a first lumen 262, a recess 264, a port 266, a second lumen 268, and a protuberance 270 and the body 324 of the cap 218 defines a first opening 326, a second opening 328, a lumen 330, and a recess 332.

The protuberance 270 is defined between the proximal end 256 and the distal end 258 of the intermediate member 214. The protuberance 270 extends outward and away from the lengthwise axis of the intermediate member 214 and has an outside diameter 271 and a thickness 273. The outside diameter 271 of the protuberance 270 is greater than the first outside diameter 259 of the intermediate member 214. The thickness 273 of the protuberance 270 extends from the proximal end of the protuberance 270 to the distal end of the protuberance 270 and can be any suitable thickness capable of releasably attaching the cap 218 to the intermediate member 214, as described in more detail herein.

Alternative to defining a protuberance 270 on the intermediate member 214, an intermediate member can define a recess between the proximal end and the distal end of the intermediate member that extends from the outer surface and toward the lengthwise axis of the intermediate member. The recess can be sized and configured to receive an o-ring that can be disposed within the recess such that a portion of the o-ring extends beyond the outer surface and away from the lengthwise axis of the intermediate member. The o-ring can be formed of a material that is relatively more flexible than the material that forms a cap (e.g., proximal end of a cap) such that the o-ring can collapse, or compress, on itself as it is passed through the first opening defined by the cap and into the recess defined by the cap. In addition, the material that forms the o-ring can expand, or return to its original structural configuration, or a configuration that is substantially similar to its original structural configuration, when it is disposed within recess defined by the cap or removed from the cap.

The recess 332 is defined between the proximal end 320 and the distal end 322 of the cap 218 within the lumen 330 defined by the cap 218. The recess 332 extends from the inner surface of the cap 218 and away from the lengthwise axis of the cap 218. The recess 332 has an inside diameter 331 that is greater than the first inside diameter 323 of the lumen 330 and a length 333. The recess 332 is sized and configured to receive the protuberance 270. The inside diameter 331 of the recess 332 is equal to the outside diameter 271 of the protuberance 270 and the length 333 of the recess 332 is equal to the thickness 273 of the protuberance 270. This configuration provides a mechanism to releasably attach the intermediate member 214 to the cap 218 using a snap fit connection between the intermediate member 214 and the cap 218. However, alternative embodiments could include a recess that has an inside diameter that is greater than, substantially equal to, or less than the outside diameter of a protuberance and/or a recess that has a length that is greater than, substantially equal to, or less than the thickness of the protuberance.

In the embodiment illustrated, the protuberance 270 defined by the intermediate member 214 is formed of a material that is relatively more flexible than the material that forms the cap 218 such that the protuberance 270 can collapse, or compress, on itself as it is passed through the first opening 326 defined by the cap 218 and into the recess 332. In addition, the protuberance 270 can expand, or return to its original structural configuration, or a configuration that is substantially similar to its original structural configuration, when it is disposed within recess 332. For example, the material that forms the protuberance 270 can have a first durometer hardness and the material that forms the cap 218 can have a second durometer hardness that is greater than the first durometer hardness. Alternatively, a portion (e.g., proximal end, portion that forms the lumen), or the entirety, of the cap can be formed of a material that is relatively more flexible than the material that forms the protuberance defined by the intermediate member such that the cap can expand and allow the protuberance to be passed through the first opening and the lumen until the protuberance is disposed within the recess defined by the cap. For example, a portion (e.g., proximal end, portion that forms the lumen), or the entirety, of the cap can be formed of a material that has a first durometer hardness and the material that forms the protuberance defined by the intermediate member can have a second durometer hardness that is greater than the first durometer hardness such that the cap can expand and allow the protuberance to be passed through the first opening and the lumen until the protuberance is disposed within the recess defined by the cap. Alternatively, a protuberance defined by an intermediate member can be formed of the same material that forms a cap and the geometry of the protuberance (e.g., outside diameter and/or thickness) is configured such that a portion of the protuberance can collapse, or compress, on itself as it is passed through the first opening defined by the cap. The material that forms the protuberance can expand, or return to its original structural configuration, or a configuration that is substantially similar to its original structural configuration, when it is disposed within the recess defined by the cap.

While an interlocking structure has been illustrated between the intermediate member 214 and the cap 218, any suitable locking structure can be included on an intermediate member and/or a cap to provide releasable attachment between the intermediate member and the cap. Skilled artisans will be able to select a suitable locking structure to include on an intermediate member and/or cap according to a particular embodiment based on various considerations, including the material(s) that forms the intermediate member and the cap. Example locking structures considered suitable include interlocking structures, structures that provide a friction fit between the elongate member and the intermediate member, morse taper configurations, threaded connections, mechanical fasteners, and any other structure considered suitable for a particular embodiment. For example, alternative to the arrangement illustrated in FIG. 5, an intermediate member can define a recess that is sized and configured to receive a protuberance defined by a cap within the lumen defined by the cap.

In use, the distal end 258 of the intermediate member 214 is positioned within sheath 216 (e.g., lumen of sheath 216) and is passed through the first opening 326 of the cap 218 and into the lumen 330 defined by the cap 218 such that the protuberance 270 is partially disposed within the recess 332. Depending on the structural configuration of the recess defined by a cap, alternative embodiments can include a protuberance that is entirely disposed within a recess defined by a cap when the two components are releasably attached to one another.

FIGS. 6 and 7 illustrate another medical device 410. The medical device 410 is similar to the medical device 10 illustrated in FIGS. 1, 2, 3, and 4 and described above, except as detailed below. Reference numbers in FIGS. 6 and 7 refer to the same structural element or feature referenced by the same number in FIGS. 1, 2, 3, and 4, offset by 400. In the embodiment illustrated, the medical device 410 comprises an elongate member 412, a sheath 416, and a cap 418.

In the illustrated embodiment, the elongate member 412 has a proximal end 424, a distal end 426, a length 427, and a body 428 that defines a proximal portion 430, a shaft 432, a first opening 540, a second opening 542, and a lumen 544.

The proximal portion 430 has a proximal end 434, a distal end 436, a length 435, a first outside diameter 437, a second outside diameter 439, and a third outside diameter 441. The length 435 of the proximal portion 430 extends from the proximal end 434 to the distal end 436 of the proximal portion 430. The first outside diameter 437 is disposed at the distal end 436 of the proximal portion 430, the second outside diameter 439 is disposed between the proximal end 434 and the distal end 436 of the proximal portion 430, and the third outside diameter 441 is disposed on the proximal end 434 of the proximal portion 430. The first outside diameter 437 and the third outside diameter 441 are greater than the second outside diameter 439. The body 428 of the elongate member 412 defines the first outside diameter 437 along a first portion 438 of the proximal portion 430, the second outside diameter 439 along a second portion 440 of the proximal portion 430, and the third outside diameter 441 along a third portion 442 of the proximal portion 430. The first portion 438 extends from the distal end 436 toward the proximal end 434 to the second portion 440 and has a length that is less than the length 435 of the proximal portion 430. The second portion 440 extends from the first portion 438 to the third portion 442 and has a length that is less than the length 435 of the proximal portion 430. The third portion 442 extends from the second portion 440 to the proximal end 434 of the proximal portion 430. The second portion 440 has a length that is greater than the length of the first portion 438 and the third portion 442.

The shaft 432 extends distally from the distal end 436 of the proximal portion 430 and has a proximal end 444, a distal end 446, and a protuberance 448. The shaft 432 has a length 445, a first outside diameter 447, a second outside diameter 449, and a third outside diameter 546. The length 445 of the shaft 432 extends from the proximal end 444 to the distal end 446 of the shaft 432. The first outside diameter 447 is disposed between the protuberance 448 and the distal end 446 of the shaft 432. The second outside diameter 449 is disposed between the first outside diameter 447 and the distal end 446 of the shaft 432, and the third outside diameter 546 is disposed at the distal end 446 of the shaft 432. The first outside diameter 447 of the shaft 432 is greater than the second outside diameter 449 of the shaft 432 and the second outside diameter 449 is greater than the third outside diameter 546 of the shaft 432. The first outside diameter 447 is less than the first outside diameter 437 of the proximal portion 430.

The body 428 of the elongate member 412 defines the first outside diameter 447 along a proximal portion 450 of the shaft 432 that extends from the protuberance 448 toward the distal end 446 of the shaft 432. The first outside diameter 447 is constant along the first portion 450 of the shaft 432. The first outside diameter 447 of the shaft 432 tapers to the second outside diameter 449 along a first tapered portion 452 of the shaft 432 that extends from the first portion 450 toward the distal end 446 of the shaft 432. The body 428 of the elongate member 412 defines the second outside diameter 449 along an intermediate portion 548 of the shaft 432 that extends from the first tapered portion 452 toward the distal end 446 of the shaft 432. The second outside diameter 449 is constant along the intermediate portion 548 of the shaft 432. The second outside diameter 449 of the shaft 432 tapers to the third outside diameter 546 along a distal portion 550 of the shaft 432 that extends from the intermediate portion 548 to the distal end 446 of the shaft 432. The body 428 of the elongate member 412 defines the third outside diameter 546 on the distal end 446 of the shaft 432. Thus, the shaft 432 has a tapered distal portion 550.

The protuberance 448 is defined between the proximal end 444 of the shaft 432 and the distal end 446 of the shaft 432. The protuberance 448 extends outward and away from the lengthwise axis of the shaft 432 and has an outside diameter 451 and a thickness 453. The outside diameter 451 of the protuberance 448 is greater than the first outside diameter 447 of the shaft 432 that extends from the protuberance 448 toward the distal end 446 of the shaft 432. The thickness 453 of the protuberance 448 extends from the proximal end of the protuberance 448 to the distal end of the protuberance 448 and can be any suitable thickness capable of releasably attaching the cap 418 to the elongate member 412, as described in more detail herein. The portion of the shaft 432 disposed between the proximal portion 430 and the protuberance 448 has an outside diameter that is less than the outside diameter 451 of the protuberance 448. In the illustrated embodiment, the portion of the shaft 432 disposed between the proximal portion 430 and the protuberance 448 has an outside diameter that is equal to the first outside diameter 447 of the shaft 432 disposed distal to the protuberance 448. However, alternative embodiments can include a portion of the shaft that is disposed between the proximal portion 430 and the protuberance 448 that has an outside diameter that is substantially equal to, less than, or greater than the first outside diameter 447 of the shaft 432 that is disposed distal to the protuberance 448. While the protuberance 448 is described as defined by the body 428 of the elongate member 412, a protuberance can alternatively be a separate component attached to the shaft of an elongate member using any suitable technique or method of attachment, such as welding, or by using adhesives.

The first opening 540 is disposed on the proximal end 424 of the elongate member 412. The second opening 542 is disposed on the distal end 426 of the elongate member 412. The lumen 544 extends from the first opening 540 to the second opening 542 and through the proximal portion 430 and the shaft 432. Each of the first opening 540, the second opening 542, and the lumen 544 has an inside diameter that is less than the second outside diameter 439 of proximal portion 430 and the second outside diameter 449 of the shaft 432. Any suitable device can be passed through the lumen 544, such as a guide wire. Alternatively, any suitable device can be disposed within the lumen defined by an elongate member.

In the illustrated embodiment, the sheath 416 is releasably disposed on the shaft 432 between the elongate member 412 and the cap 418. The sheath 416 comprises a proximal end 486, a distal end 488, and a body 490. The sheath 416 has a length 487 that extends from the proximal end 486 to the distal end 488 and is less than the length 445 of shaft 432. The body 490 of the sheath 416 defines a first opening 492, a second opening 494, a lumen 496, a flared proximal portion 498, a tapered distal portion 500, and a passageway 502. The first opening 492 is defined on the proximal end 486 and the second opening 494 is defined on the distal end 488. The lumen 496 extends from the first opening 492 to the second opening 494.

The first opening 492 has a first inside diameter 489 and the second opening 494 has a second inside diameter 491. Thus, the lumen 496 has a first inside diameter 489 and a second inside diameter 491. The first inside diameter 489 is greater than the second inside diameter 491 and is greater than the first outside diameter 447 of the shaft 432. The second inside diameter 491 is greater than the second outside diameter 449 of the shaft 432. Alternatively, the second inside diameter of a sheath can be equal to, substantially equal to, or less than the second outside diameter of a shaft such that a friction fit between the sheath and shaft can be accomplished. The first inside diameter 489 extends along a proximal portion 552 of the lumen 496 that extends from the proximal end 486 toward the distal end 488 of the sheath 416. The proximal portion 552 of lumen 496 is barrel-shaped and is sized and configured to receive a portion of elongate member 412 (e.g., proximal portion 450 and/or first tapered portion 452). The first inside diameter 489 tapers to the second inside diameter 491 along a tapered portion 554 of the lumen 496 that extends from the proximal portion 552 toward the distal end 488 to a location between the proximal end 486 and the distal end 488. The proximal portion 552 and the tapered portion 554 of the lumen 496 have a structural arrangement that is complementary to the structural arrangement of the proximal portion 450 and the first tapered portion 452 defined by the elongate member 412. The second inside diameter 491 extends along a distal portion 556 of the lumen 496 that extends from the tapered portion 554 to the distal end 488 of the sheath 416.

In the illustrated embodiment, the sheath 416 has a first outside diameter 497, a second outside diameter 499, and a third outside diameter 501. The first outside diameter 497 is disposed on the proximal end 486, the second outside diameter 499 is disposed between the proximal end 486 and the distal end 488, and the third outside diameter 501 is disposed on the distal end 488. The first outside diameter 497 is greater than the second outside diameter 499 and is disposed proximal to the second outside diameter 499. The second outside diameter 499 is greater than the third outside diameter 501 and is disposed proximal to the third outside diameter 501. The first outside diameter 497 extends along a proximal portion 506 of the sheath 416 that extends from the proximal end 486 toward the distal end 488. The first outside diameter 497 tapers to the second outside diameter 499 along a tapered portion 508 of the sheath 416 that extends from the proximal portion 506 toward the distal end 488. The proximal portion 506 and the tapered portion 508 cooperatively define a barrel-shaped flared proximal portion 498 that acts as a mechanical stop to distal advancement of the sheath 416 beyond tissue disposed outside of a bodily passage (e.g., the flared proximal portion contacts tissue disposed outside of a bodily passage). The second outside diameter 499 extends along an intermediate portion 510 of the sheath 416 that extends from the tapered portion 508 toward the distal end 488. The second outside diameter 499 tapers to the third outside diameter 501 along a distal portion 512 of the sheath 416 and defines the tapered distal portion 500.

The passageway 502 is disposed on the flared proximal portion 498 of sheath 416 between the proximal end 486 and the distal end 488 of the sheath 416. The passageway 502 extends through the body 490 of the sheath 416 and provides access to lumen 496. The passageway 502 has a diameter that is sized and configured to receive a suture, or one or more lengths of a suture. The passageway 502 can have any suitable structural arrangement. For example, a passageway can have a structural arrangement that defines any suitable geometric shape, such as a cylinder, cuboid, cube, triangular prism, sphere, semi-sphere, and any other structural arrangement considered suitable for a particular embodiment. In the illustrated embodiment, the passageway 502 is cylindrical.

In the illustrated embodiment, the body 524 of the cap 418 defines a first opening 526, a second opening 528, a first lumen 530, a recess 532, a port 560, a third opening 562, a fourth opening 564, and a second lumen 566.

The recess 532 is defined between the proximal end 520 and the distal end 522 of the cap 418 within the lumen 530 defined by the cap 418. The recess 532 has an inside diameter 531 that is greater than the first inside diameter 523 of the lumen 530 and a length 536. The recess 532 is sized and configured to receive the protuberance 448 defined by the elongate member 412. The inside diameter 531 of the recess 532 is equal to the outside diameter 451 of the protuberance 448 and the length 536 of the recess 532 is equal to the thickness 453 of the protuberance 448. This configuration provides a mechanism to releasably attach the elongate member 412 to the cap 418 using a snap fit connection between the elongate member 412 and the cap 418. However, alternative embodiments could include a recess that has an inside diameter that is greater than, substantially equal to, or less than the outside diameter of a protuberance and/or a recess that has a length that is greater than, substantially equal to, or less than the thickness of the protuberance.

In the embodiment illustrated, the protuberance 448 defined by the elongate member 414 is formed of a material that is relatively more flexible than the material that forms the cap 418 such that the protuberance 448 can collapse, or compress, on itself as it is passed through the first opening 526 defined by the cap 418 and into the recess 532. In addition, the protuberance 448 can expand, or return to its original structural configuration, or a configuration that is substantially similar to its original structural configuration, when it is disposed within recess 532. For example, the material that forms the protuberance 448 can have a first durometer hardness and the material that forms the cap 418 can have a second durometer hardness that is greater than the first durometer hardness. Alternatively, a portion (e.g., proximal end, portion that forms the lumen), or the entirety, of the cap can be formed of a material that is relatively more flexible than the material that forms the protuberance defined by the elongate member such that the cap can expand and allow the protuberance to be passed through the first opening and the lumen until the protuberance is disposed within the recess defined by the cap. For example, a portion (e.g., proximal end, portion that forms the lumen), or the entirety, of the cap can be formed of a material that has a first durometer hardness and the material that forms the protuberance defined by the elongate member can have a second durometer hardness that is greater than the first durometer hardness such that the cap can expand and allow the protuberance to be passed through the first opening and the lumen until the protuberance is disposed within the recess defined by the cap. Alternatively, a protuberance defined by an elongate member can be formed of the same material that forms a cap and the geometry of the protuberance (e.g., outside diameter and/or thickness) is configured such that a portion of the protuberance can collapse, or compress, on itself as it is passed through the first opening defined by the cap. The material that forms the protuberance can expand, or return to its original structural configuration, or a configuration that is substantially similar to its original structural configuration, when it is disposed within the recess defined by the cap.

While an interlocking structure has been illustrated between the elongate member 412 and the cap 418, any suitable locking structure can be included on an elongate member and/or a cap to provide releasable attachment between the elongate member and the cap. Skilled artisans will be able to select a suitable locking structure to include on an elongate member and/or cap according to a particular embodiment based on various considerations, including the material(s) that forms the elongate member and the cap. Example locking structures considered suitable include interlocking structures, structures that provide a friction fit between the elongate member and the cap, morse taper configurations, threaded connections, mechanical fasteners, and any other structure considered suitable for a particular embodiment. For example, alternative to the arrangement illustrated in FIGS. 6 and 7, an elongate member can define a recess that is sized and configured to receive a protuberance defined by a cap within the lumen defined by the cap.

The port 560 is disposed between the proximal end 520 and the distal end 522 of the cap 418. The third opening 562 is defined on the port 560 and the fourth opening 564 is defined between the proximal end 520 and the distal end 522 of the cap 418 and is in fluid communication with the first lumen 530 defined by the cap 418. The second lumen 566 extends from the third opening 562 to the fourth opening 564 and is in fluid communication with the first lumen 530. Port 560 provides a mechanism for providing treatment via the second lumen 566 when the elongate member 412 has been withdrawn from the cap 418, such as by applying suction to the second lumen 566 using a suction device attached to the port 560 or that is in communication with the second lumen 566.

The port 560 can include any suitable connector and/or adapter capable of attaching one or more devices to the cap 418. Skilled artisans will be able to select a suitable connector and/or adapter to include on a port of a cap according to a particular embodiment based on various considerations, including the material(s) that forms the cap. Example connectors and/or adapters considered suitable to include on a port of a cap include threaded connectors, Tuohy Borst adapters, luer lock connectors, and any other connector and/or adapter considered suitable for a particular embodiment.

In use, the distal end 488 of the sheath 416 is passed through the first opening 526 of the cap 418 and into the lumen 530 defined by the cap 418 such that the flared proximal portion 498 is disposed within the first lumen 530 defined by the cap 418. For example, the sheath 416 can be advanced into the lumen 530 defined by the cap 418 until the outer surface of the sheath 416 (e.g., proximal portion 498) contacts the inner wall of the cap 418 (e.g., tapered portion 534). Subsequently, the distal end 426 of the elongate member 412 is passed through the lumen 496 defined by the sheath 416 and the protuberance 448 is partially disposed within the recess 532 defined by the cap 418. Depending on the structural configuration of the recess defined by a cap, alternative embodiments can include a protuberance that is entirely disposed within a recess defined by a cap when the elongate member and cap are releasably attached to one another. The elongate member 412 can be optionally be advanced into the lumen 496 defined by the sheath 416 until the outer surface of the elongate member 412 (e.g., tapered portion 452) contacts the inner wall of the sheath 416 and the outer wall of the sheath 416 contacts the inner wall of the cap 418 (e.g., tapered portion 554) and compresses, or pinches, the sheath 416 between the elongate member 412 and the cap 418, as shown in FIG. 6. This provides a mechanism for advancing the sheath 416 into a bodily passage.

In the embodiment illustrated, the sheath 416 is formed of a material that is relatively more flexible than the material that forms the cap 418 such that the sheath 416 can collapse, or compress, on itself as it is passed in a distal direction through the first lumen 530 defined by the cap 418. Once the sheath 416 is free of the cap 418, the sheath 416 can expand, or return to its original structural configuration, or a configuration that is substantially similar to its original structural configuration. For example, the sheath 416 can be formed of a material that has a first durometer hardness and the material that forms the cap 418 can have a second durometer hardness that is greater than the first durometer hardness. Alternatively, a portion (e.g., distal end, portion that forms the lumen of the cap), or the entirety, of the cap can be formed of a material that is relatively more flexible than the material that forms the sheath such that the cap can expand and allow the sheath to be passed through the lumen defined by the cap until the sheath is free of the cap. For example, a portion (e.g., distal end, portion that forms the lumen of the cap), or the entirety, of the cap can be formed of a material that has a first durometer hardness and the material that forms the sheath can have a second durometer harness that is greater than the first durometer hardness such that the cap can expand and allow the sheath to be passed through the lumen defined by the cap until the sheath is free of the cap. Alternatively, a sheath can be formed of the same material that forms a cap and the geometry of the sheath (e.g., thickness of sheath) is configured such that a portion of the sheath can collapse, or compress, on itself as it is passed through the second opening defined by the cap. The material that forms the sheath can expand, or return to its original structural configuration, or a configuration that is substantially similar to its original structural configuration, when it is free of the cap.

FIGS. 8 and 9 illustrates another medical device 610. The medical device 610 is similar to the medical device 10 illustrated in FIGS. 1, 2, 3, and 4 and described above, except as detailed below. Reference numbers in FIGS. 8 and 9 refer to the same structural element or feature referenced by the same number in FIGS. 1, 2, 3, and 4, offset by 600. In the embodiment illustrated, the medical device 610 comprises an elongate member 612, an intermediate member 614, and a sheath 616. The intermediate member 614 is moveable between a first configuration and a second configuration, as described in more detail herein.

In the illustrated embodiment, the elongate member 612 defines threads 648 between the proximal end 644 and the distal end 646 of the shaft 632. Threads 648 have a helical configuration that is sized and configured to interact with the helical configuration defined by threads 664 defined by the intermediate member 616, as described herein. For example, the threads 648 defined by the elongate member 612 are sized and configured to mate with the threads 664 defined by the intermediate member 616 such that the elongate member 612 is releasably attached to the intermediate member 614 using threads 648 and threads 664. Threads 648 provide a mechanism to releasably attach the elongate member 612 to the intermediate member 614.

In the illustrated embodiment, the intermediate member 614 defines threads 664 within first lumen 662, a track 770, a first slot 772, a second slot 774, a cavity 776, and includes a sleeve 778. The intermediate member 614 is moveable between a first configuration in which the sheath 616 is free of attachment to the intermediate member 614, as shown in FIG. 8, and a second configuration in which the sheath 616 is releasably attached to the intermediate member 614, as shown in FIG. 9.

The intermediate member 614 defines threads 664 between the proximal end 656 and the distal end 658 of the intermediate member 614 within the first lumen 662. Threads 664 have a helical configuration that is sized and configured to interact with the helical configuration defined by threads 648 defined by the elongate member 612. For example, the threads 664 defined by the intermediate member 614 are sized and configured to mate with the threads 648 defined by the elongate member 612 such that the elongate member 612 is releasably attached to the intermediate member 614 using threads 648 and threads 664. Threads 664 provide a mechanism to releasably attach the intermediate member 614 to the elongate member 612.

The track 770 comprises a recessed intermediate portion of the intermediate member 614 that is disposed between the proximal end 656 and the distal end 658 of the intermediate member 614. The track 770 has a first outside diameter at the proximal end of the track 770 and a second outside diameter at the distal end of the track 770. The second outside diameter of the track 770 is greater than the first outside diameter of the track 770. Thus, the track 770 has an outside diameter that increases from the proximal end to the distal end of the track 770. The first slot 772 extends from a first opening on the distal end 658 of the intermediate member 614 toward the proximal end 656 of the intermediate member 614. The second slot 774 extends from a second opening on the distal end 658 of the intermediate member 614 toward the proximal end 656 of the intermediate member 614. The cavity 776 extends into the body 660 of the intermediate member 614 from a circumferential opening defined on the distal end 658 of the intermediate member 614 and toward the proximal end 656 of the intermediate member 614. The cavity 776 is sized and configured to receive a proximal portion of the sheath 616, as shown in FIG. 9.

The sleeve 778 is disposed within the track 770 and is moveable from a first position to a second position. FIG. 8 shows the sleeve 778 in the first position and FIG. 9 shows the sleeve 778 in the second position. In the first position, the sleeve 778 is disposed at, or near, the proximal end of the track 770 and the intermediate member 614 is in the first configuration. In the second position, the sleeve 778 is disposed at, or near, the distal end of the track 770 and the intermediate member 614 is in the second configuration. Movement of the sleeve 778 from the first position to the second position decreases the outside diameter of the distal end of the intermediate member 614 and releasably attaches the sheath 616 to the intermediate member 614. Movement of the sleeve 778 from the second position to the first position increases the outside diameter of the distal end of the intermediate member 614 and releases the sleeve 616 from attachment to the intermediate member 616.

The track 770, first slot 772, second slot 774, cavity 776, and the sleeve 778 cooperatively create a collet configuration that can be used to releasably attach the sheath 616 to the intermediate member 614.

In the illustrated embodiment, the sheath 616 has a first outside diameter 697, a second outside diameter 699, and a third outside diameter 701. The first outside diameter 697 is disposed on the proximal end 686, the second outside diameter 699 is disposed between the proximal end 686 and the distal end 688, and the third outside diameter 701 is disposed on the distal end 688. The first outside diameter 697 is greater than the second outside diameter 699 and is disposed proximal to the second outside diameter 699. The second outside diameter 699 is greater than the third outside diameter 701 and is disposed proximal to the third outside diameter 701. The first outside diameter 697 extends along a proximal portion 706 of the sheath 616 that extends from the proximal end 686 toward the distal end 688. The first outside diameter 697 tapers to the second outside diameter 699 along a tapered portion 708 of the sheath 616 that extends from the proximal portion 706 toward the distal end 688 and defines the flared proximal portion 698. The flared proximal portion 698 acts as a mechanical stop to distal advancement of the sheath 616 beyond tissue disposed outside of a bodily passage (e.g., the flared proximal portion contacts tissue disposed outside of a bodily passage). The flared proximal portion 698 is barrel-shaped and tapers from the first outside diameter 697 to the second outside diameter 699. The second outside diameter 699 extends along an intermediate portion 710 of the sheath 616 that extends from the tapered portion 708 toward the distal end 688. The second outside diameter 699 tapers to the third outside diameter 701 along a distal portion 712 of the sheath 716 and defines the tapered distal portion 700.

The passageway 702 is disposed on the flared proximal portion 698 of sheath 616 between the proximal end 686 and the distal end 688 of the sheath 616. The passageway 702 extends through the body 690 of the sheath 616 and provides access to lumen 696. The passageway 702 has a diameter that is sized and configured to receive a suture, or one or more lengths of a suture. The passageway 702 can have any suitable structural arrangement. For example, a passageway can have a structural arrangement that defines any suitable geometric shape, such as a cylinder, cuboid, cube, triangular prism, sphere, semi-sphere, and any other structural arrangement considered suitable for a particular embodiment. In the illustrated embodiment, the passageway 702 is cylindrical.

Various methods of treatment are described herein. While the methods described herein are shown and described as a series of acts, it is to be understood and appreciated that the methods are not limited by the order of acts, as some acts may in accordance with these methods, occur in different orders, and/or concurrently with other acts described herein.

Figure 10:
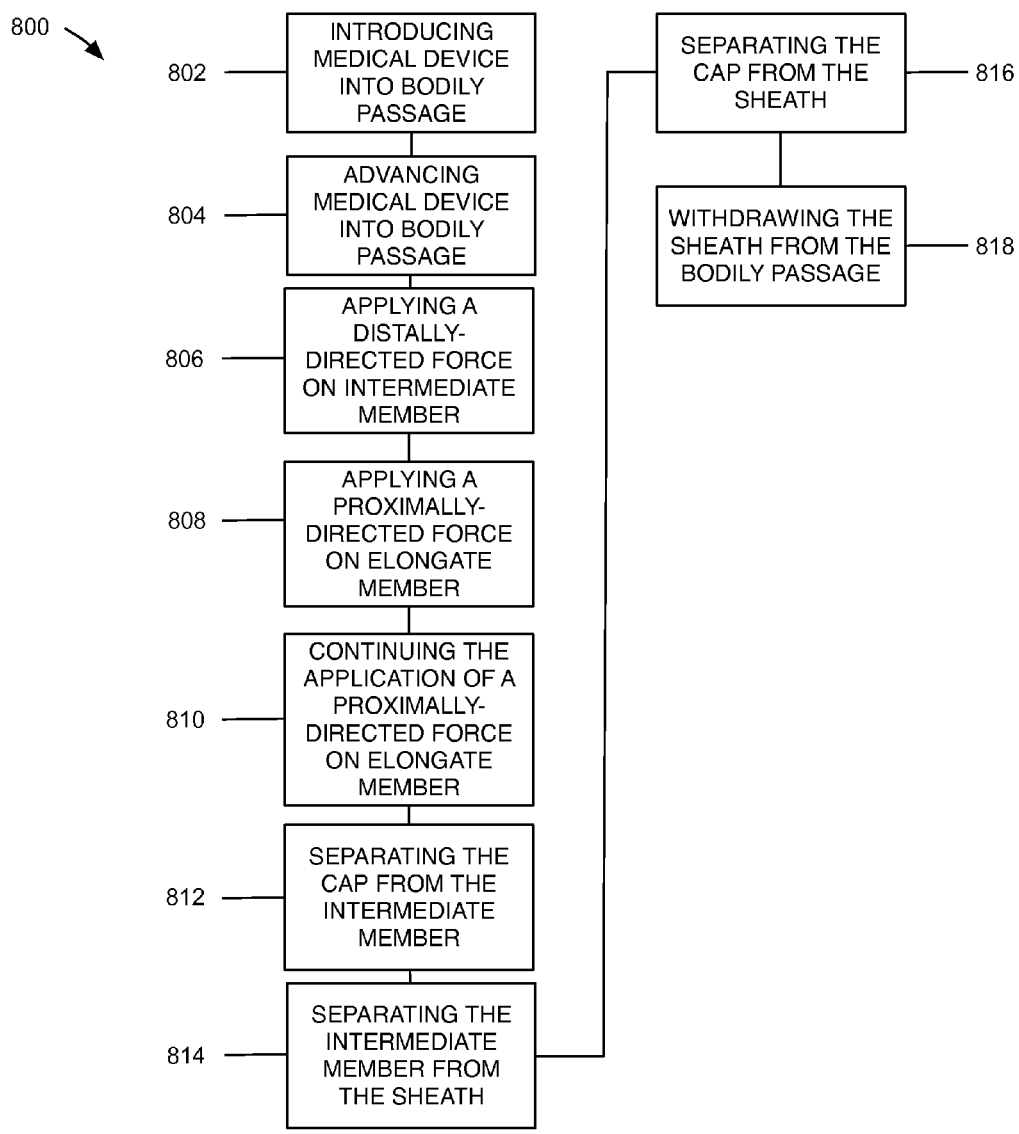
FIG. 10 is a flowchart representation of an example method of treatment.

FIG. 10 is a flowchart representation of a method 800 of treating a bodily passage.

A step 802 comprises introducing a medical device having a medical device proximal end and a medical device distal end into a bodily passage such that the medical device distal end is disposed within the bodily passage. The bodily passage is defined by a bodily passage wall. Another step 804 comprises advancing the medical device into the bodily passage until the second outside diameter of the sheath is disposed within the bodily passage. Another step 806 comprises applying a distally-directed force on the intermediate member. Another step 808 comprises applying a proximally-directed force on the elongate member while applying a distally-directed force on the intermediate member such that the elongate member is advanced proximally relative to the sheath. Another step 810 comprises continuing the application of a proximally-directed force on the elongate member while applying a distally-directed force on the intermediate member until the elongate member is free of the sheath. Another step 812 comprises separating the cap from the intermediate member. Another step 814 comprises separating the intermediate member from the sheath. Another step 816 comprises separating the cap from the sheath. Another step 818 comprises withdrawing the sheath from the bodily passage.

Step 802 can be accomplished using any suitable medical device according to an embodiment, such as the embodiments described and illustrated herein. Skilled artisans will be able to select a suitable medical device to introduce into a bodily passage according to a particular embodiment based on various considerations, including the treatment intended to be performed. Examples of medical devices considered suitable to introduce into a bodily passage to complete one or more steps and/or methods described herein include medical device 10, medical device 210, medical device 410, medical device 610, medical devices that include the alternative components described herein (e.g., intermediate member 14'), and any other medical device considered suitable for a particular application.

Step 802 can be accomplished by introducing a medical device into any suitable bodily passage. Skilled artisans will be able to select a suitable bodily passage to introduce a medical device according to a particular embodiment based on various considerations, including the treatment intended to be performed. Example bodily passages considered suitable to introduce a medical device include a salivary duct, a portion of the urinary tract, and any other bodily passage considered suitable for a particular application.

An optional step that can be completed prior to step 802 comprises hydrating the sheath of the medical device. This can be accomplished using any suitable technique (e.g., applying liquid to sheath) and material, such as saline.

Step 804 can be accomplished by applying a distally-directed force (e.g., toward the bodily passage) on any suitable portion of the medical device such that the medical device is advanced into the bodily passage and the second outside diameter of the sheath is disposed within the bodily passage. For example, a distally-directed force can be applied on an elongate member of an embodiment, such as elongate member 12, elongate member 212, elongate member 412, or elongate member 612.

An optional step comprises advancing the medical device into the bodily passage such that the tapered distal portion of the cap contacts tissue disposed outside of the bodily passage. This step can be accomplished by placing a distally-directed force (e.g., toward the bodily passage) on any suitable portion of the medical device until the distal surface of the cap contacts the tissue disposed outside of the bodily passage. Alternatively, if the medical device omits the inclusion of a cap (e.g., medical device 610) an optional step comprises advancing the medical device into the bodily passage such that the distal surface of the intermediate member contacts tissue disposed outside of the bodily passage. This step can be accomplished by placing a distally-directed force (e.g., toward the bodily passage) on any suitable portion of the medical device until the distal surface of intermediate member contacts the tissue disposed outside of the bodily passage.

Step 806 can be accomplished by applying a distally-directed force on the intermediate member such that the intermediate member is advanced toward the tissue disposed outside of the bodily passage. The distally-directed force can be applied to any suitable portion of an intermediate member, such as the outside perimeter, or edge, of the intermediate member, and/or the proximal surface of an intermediate member. Alternative to applying a distally-directed force on the intermediate member, an alternative step comprises maintaining the position of the intermediate member relative to the elongate member. This step can be accomplished by applying any suitable force (e.g., a force directed radially inward) on the intermediate member such that the position of the intermediate member is maintained relative to the elongate member, the tissue disposed outside of the bodily passage, and/or the bodily passage.

Alternatively, if the medical device omits the inclusion of an intermediate member (e.g., medical device 410), an alternative step comprises applying a distally-directed force on the cap such that the cap is advanced toward and/or contacts the tissue disposed outside of the bodily passage. The distally-directed force can be applied to any suitable portion of a cap, such as the outside perimeter, or edge, of the cap, and/or the proximal surface of a cap. Alternative to applying a distally-directed force on the cap, an alternative step comprises maintaining the position of the cap relative to the elongate member. This step can be accomplished by applying any suitable force (e.g., a force directed radially inward) on the cap such that the position of the cap is maintained relative to the elongate member, the tissue disposed outside of the bodily passage, and/or the bodily passage Step 808 can be accomplished by applying a proximally-directed force (e.g., away from the bodily passage) on any suitable portion of the elongate member (e.g., proximal portion) while applying a distally-directed force on the intermediate member such that the elongate member is advanced proximally relative to the intermediate member and sheath and is advanced proximally through the lumen defined by the sheath. For example, step 808 can be accomplished concurrently with step 806. Alternative to applying a proximally-directed force on the elongate member while applying a distally-directed force on the intermediate member, an alternative step comprises applying a proximally-directed force (e.g., away from the bodily passage) on the elongate member while maintaining the position of the intermediate member relative to the sheath such that the elongate member is advanced proximally relative to the intermediate member and the sheath and is advanced proximally through the lumen defined by the sheath.

Alternatively, if the medical device omits the inclusion of an intermediate member (e.g., medical device 410), an alternative step comprises applying a proximally-directed force (e.g., away from the bodily passage) on any suitable portion of the elongate member (e.g., proximal portion) while applying a distally-directed force on the cap such that the elongate member is advanced proximally relative to the cap and sheath and is advanced proximally through the lumen defined by the cap. For example, this step can be accomplished concurrently with the alternative step described above. Alternative to applying a proximally-directed force on the elongate member while applying a distally-directed force on the cap, an alternative step comprises applying a proximally-directed force (e.g., away from the bodily passage) on the elongate member while maintaining the position of the cap relative to the elongate member such that the elongate member is advanced proximally relative to the cap and the elongate member and is advanced proximally through the lumen defined by the sheath.

Step 810 can be accomplished by continuing the application of a proximally-directed force on the elongate member while applying a distally-directed force on the intermediate member until the distal end of the shaft is disposed proximal to the proximal end of the intermediate member and the elongate member is free of the sheath and the intermediate member. Alternative to continuing the application of a proximally-directed force on the elongate member while applying a distally-directed force on the intermediate member, an alternative step comprises continuing the application of a proximally-directed force on the elongate member while maintaining the position of the intermediate member relative to the sheath until the distal end of the shaft is disposed proximal to the proximal end of the intermediate member and the elongate member is free of the intermediate member and the sheath.

Alternatively, if the medical device omits the inclusion of an intermediate member (e.g., medical device 410), an alternative step comprises continuing the application of a proximally-directed force on the elongate member while applying a distally-directed force on the cap until the distal end of the shaft is disposed proximal to the proximal end of the cap and the elongate member is free of the sheath and the cap. Alternative to continuing the application of a proximally-directed force on the elongate member while applying a distally-directed force on the cap, an alternative step comprises continuing the application of a proximally-directed force on the elongate member while maintaining the position of the cap relative to the sheath until the distal end of the shaft is disposed proximal to the proximal end of the cap and the elongate member is free of the cap and the sheath.

An optional step that can be completed after the elongate member has been removed from the lumen defined by the sheath comprises attaching a tubular member to a port defined by an intermediate member or a cap such that treatment can be performed. For example, treatment can include attaching the tubular member to a suction device such that suction can be applied to the lumen defined by the intermediate member, cap, and/or sheath.

Another optional step that can be completed after the elongate member has been removed from the lumen defined by the sheath comprises passing a medication and/or medical device through the lumen defined by the sheath and into the bodily passage to perform treatment. Alternatively, a medical device can be passed through a portion of the lumen defined by the sheath. This step can be accomplished using any suitable medication and/or medical device, and skilled artisans will be able to select a suitable medication and/or medical device to pass through the entirety, or a portion, of a sheath according to a particular embodiment based on various considerations, including the treatment intended to be performed. Example medical devices considered suitable to pass through the lumen defined by a sheath include dilators, scopes, suction catheters, balloon catheters, irrigation catheters, a camera, a light source, baskets, cutting devices, and any other medical device considered suitable for a particular application. Another optional step comprises performing treatment with a medical device that has been passed through a portion, or the entirety, of the lumen defined by the sheath. Another optional step comprises withdrawing the medical device from the lumen defined by the sheath. Any suitable treatment can be performed, such as treatment of one or more strictures within the bodily passage and/or removing one or more stones disposed within the bodily passage.

In embodiments in which intermediate member 14' is included in the medical device (e.g., medical device 10), another optional step that can be completed subsequent to step 810 comprises separating the first member from the second member. This optional step can be completed by applying a proximal force on the second member while maintaining the position of the first member, applying a proximal force on the second member while applying a distal force on the first member, or by maintaining the position of the second member and applying a distal force on the first member until the second member is free of attachment to the first member.

When medical device 10 is being used to complete method 800, step 812 can be accomplished by applying a rotational force on the intermediate member while maintaining the position of the cap, applying a first rotational force on the intermediate member and a second opposite rotational force on the cap, or maintaining the position of the intermediate member and applying a rotation force on the cap until the intermediate member is free of the cap. When medical device 210 is being used to complete method 800, step 812 can be accomplished by applying a proximally-directed force on the intermediate member while maintaining the position of the cap, applying a proximally-directed force on the intermediate member and a distally-directed force on the cap, or maintaining the position of the intermediate member and applying a distally-directed force on the cap until the intermediate member is free of the cap. If medical device 410 is being used to complete method 800, step 812 can be omitted from method 800 because medical device 410 does not include an intermediate member. If medical device 610 is being used to complete method 800, step 812 can be omitted from method 800 because medical device 410 does not include a cap.

Step 814 can be accomplished by applying a proximally-directed force on any suitable portion of the intermediate member such that the intermediate member is free of the sheath. If medical device 410 is being used to complete method 800, step 814 can be omitted from method 800 because medical device 410 does not include an intermediate member. If medical device 610 is being used to complete method 800, an optional step that can be accomplished prior to step 814 comprises advancing the sleeve from the second position to the first position such that the intermediate member moves from the second configuration to the first configuration. Another optional step that can be completed prior to, concurrent with, or subsequent to, step 804 comprises positioning the sheath within the cavity defined by the intermediate member and advancing the sleeve from the first position to the second position such that the intermediate member moves from its first configuration to its second configuration.

An optional step comprises applying a distally-directed force (e.g., toward the bodily passage) on the sheath such that the sheath contacts the tissue outside of the bodily passage or that forms the bodily passage wall.

Step 816 can be accomplished by applying a proximally-directed force on the cap while maintaining the position of the sheath such that the sheath is advanced through the lumen of the cap, as shown in FIG. 4, and exits through the distal opening defined by the cap. Alternatively, step 816 can be accomplished by applying a proximally-directed force on the cap while applying a distally-directed force on the sheath such that the sheath is advanced through the lumen of the cap and exits through the distal opening defined by the cap. Alternatively, step 816 can be accomplished by maintaining the position of the cap while applying a distally-directed force on the sheath such that the sheath is advanced through the lumen of the cap and exits through the distal opening defined by the cap. If medical device 610 is being used to complete method 800, step 816 can be omitted from method 800 because medical device 410 does not include a cap.

Step 818 can be accomplished by applying a proximally-directed force on the sheath until it has been withdrawn from the bodily passage such that the distal end of the sheath is disposed proximal to the bodily passage. Optionally, step 818 can be omitted from method 800. For example, step 818 can be omitted in embodiments in which the sheath is formed of a biodegradable or bioabsorbable material.

An optional step that can be completed prior to withdrawing the sheath from the bodily passage comprises suturing the sheath to tissue that is disposed outside of the bodily passage. This step can be accomplished by passing a suture through a passageway defined by the sheath and through the tissue that is disposed outside of the bodily passage to secure the sheath to the tissue and within the bodily passage. In embodiments in which the body of the sheath defines more than one passageway, an optional step than can be completed prior to withdrawing the sheath from the bodily passage comprises passing a suture through each passageway, or one or more of the passageways, and through the tissue that is disposed outside of the bodily passage to secure the sheath to the wall that defines the bodily passage.

A step that can be completed in addition to, or alternative to, the optional steps described above and prior to withdrawing the sheath from the bodily passage comprises suturing the sheath to the wall that defines the bodily passage. This step can be accomplished by passing a suture through a passageway defined by the sheath and through the bodily passage wall to secure the sheath to the bodily passage wall and within the bodily passage. In embodiments in which the body of the sheath defines more than one passageway, this step can comprise passing a suture through each passageway, or one or more of the passageways, and through the bodily passage wall to secure the sheath to the bodily passage wall.

An optional step that can be completed prior to withdrawing the sheath from the bodily passage comprises leaving the sheath in the bodily passage for an interval of time. For example, a sheath can be disposed within a bodily passage such that the lumen defined by the sheath can be utilized as a drain for any material disposed within the bodily passage (e.g., the material disposed within the bodily passage can pass through the lumen defined by the sheath to an environment exterior to the bodily passage). Any suitable interval of time is considered suitable, and skilled artisans will be able to select a suitable interval of time to leave a sheath in a bodily passage according to a particular embodiment based on various considerations, including the treatment intended to be performed. Example intervals of time considered suitable to leave a sheath within a bodily passage include one or more minutes, one or more hours, one or more days, and any other interval of time considered suitable for a particular application.

Another optional step that can be completed prior to withdrawing the sheath from the bodily passage comprises passing a medication and/or medical device through the lumen defined by the sheath and into the bodily passage to perform treatment. Alternatively, a medical device can be passed through a portion of the lumen defined by the sheath. This step can be accomplished using any suitable medication and/or medical device, and skilled artisans will be able to select a suitable medication and/or medical device to pass through the entirety, or a portion, of a sheath according to a particular embodiment based on various considerations, including the treatment intended to be performed. Example medical devices considered suitable to pass through the lumen defined by a sheath include suction catheters, balloon catheters, irrigation catheters, a camera, a light source, and any other medical device considered suitable for a particular application. Another optional step comprises performing treatment with a medical device that has been passed through a portion, or the entirety, of the lumen defined by the sheath. Another optional step comprises withdrawing the medical device from the lumen defined by the sheath.

Optionally, in embodiments in which the elongate member defines a lumen that extends through its length (e.g., elongate member 410) an optional step that can be completed prior to step 802 comprises introducing a guide wire that has a guide wire proximal end and a guide wire distal end into a bodily passage such that the guide wire distal end is disposed within the bodily passage. This optional step can be accomplished using any suitable guide wire having any suitable length and structural arrangement. Skilled artisans will be able to select a guide wire to introduce into a bodily passage according to a particular embodiment based on various considerations, including the treatment intended to be performed. This optional step can be accomplished by applying a distally-directed force on any suitable portion of the guide wire such that the guide wire distal end is advanced into the bodily passage. This optional step can be accomplished by introducing a guide wire into any suitable bodily passage. Skilled artisans will be able to select a suitable bodily passage to introduce a guide wire according to a particular embodiment based on various considerations, including the treatment intended to be performed. Example bodily passages considered suitable to introduce a guide wire include a salivary duct, a portion of the urinary tract, and any other bodily passage considered suitable for a particular application.

If a guide wire is used to complete method 800, another optional step comprises advancing the medical device over the guide wire such that the guide wire is disposed within a lumen defined by an elongate member of the medical device. This optional step can be accomplished using any suitable medical device according to an embodiment, such as the embodiments described and illustrated herein. Skilled artisans will be able to select a suitable medical device to advance over a guide wire according to a particular embodiment based on various considerations, including the treatment intended to be performed. Examples of medical devices considered suitable to advance over a guide wire to complete one or more steps and/or methods described herein include medical devices that include an elongate member that defines a lumen that extends from the proximal end of the elongate member to the distal end of the elongate member (e.g., elongate member 410). Any of the medical devices described and illustrated herein, such as medical device 10, medical device 210, medical device 410, medical device 610, are considered suitable and can include an elongate member that defines a lumen that extends from the proximal end of the elongate member to the distal end of the elongate member. This optional step can be accomplished by passing the proximal end of the guide wire through a distal opening of the lumen defined by the elongate member (e.g., lumen 544 of elongate member 412) and applying a distally-directed force on any suitable portion of the medical device such that the guide wire is passed through the a proximal opening of the lumen and the medical device is disposed on the guide wire.

If a guide wire is used to complete method 800, another optional step comprises withdrawing the guide wire from the bodily passage and the medical device. This optional step can be accomplished by applying a proximally-directed force on any suitable portion of the guide wire such that the guide wire is withdrawn from the bodily passage and the lumen defined by the elongate member.

FIG. 11 illustrates another intermediate member 14'. The intermediate member 14' is similar to the intermediate member 14 illustrated in FIGS. 1, 2, 3, and 4 and described above, except as detailed below. Reference numbers in FIG. 11 refer to the same structural element or feature referenced by the same number in FIGS. 1, 2, 3, and 4, offset by '. In the embodiment illustrated, the intermediate member 14' comprises a first member 15', a second member 17', a proximal end 21', and a distal end 23'. The first member 15' and the second member 17' are moveable between a first configuration in which the first member 15' is releasably attached to the second member 17' and a second configuration in which the first member 15' is free of the second member 17'. FIG. 11 illustrates the intermediate member 14' in the second configuration. When included in a medical device, such as medical device 10 illustrated in FIGS. 1, 2, 3, and 4, intermediate member 14' can be releasably attached to the elongate member 12 between the elongate member 12 (e.g., proximal portion 30) and the sheath 16.

In the illustrated embodiment, the first member 15' comprises a proximal end 56', a distal end 58', and a body 60'. The first member 15' has a length 57', a first outside diameter 59', a second outside diameter 61', and a third outside diameter 63'. The length 57' extends from the proximal end

56' to the distal end 58' of the first member 15'. The body 60' of the first member 15' defines a first lumen 62', a recess 64', a port 66', a second lumen 68', and threads 70'.

The first outside diameter 59' is greater than the first outside diameter of the proximal portion (e.g., first outside diameter 37). The first outside diameter 59' extends along a proximal portion 82' of the first member 15' that extends from the proximal end 56' toward the distal end 58'. The second outside diameter 61' is equal to the first outside diameter 59' and extends from the recess 64' toward the distal end 58'. Alternatively, the second outside diameter can be substantially equal to, greater than, or less than the first outside diameter of a first member. The third outside diameter 63' is disposed on the distal end 58' of the first member 15' and is less than the second outside diameter 61'. The first member 15' has an outer surface that defines a tapered portion 84' that extends between the port 66' and the distal end 58'. However, alternative embodiments can include a tapered portion that extends from the distal end toward the proximal end of a first member. The tapered portion 84' tapers from the second outside diameter 61' to the third outside diameter 63'. The tapered portion 84' is sized and configured such that a portion of the tapered portion 84' can be received by a sheath, as described in more detail herein. Thus, the tapered portion 84' corresponds to the structural arrangement of the proximal portion of a lumen defined by a sheath.

The first lumen 62' extends from a first opening 72' defined on the proximal end 56' of the first member 15' to a second opening 74' defined on the distal end 58' of the first member 15'. The recess 64' is defined between the proximal end 56' and the distal end 58' of the first member 15' and has an inside diameter 65' and a length 67'. The recess 64' extends from the outer surface of the first member 15' and toward the lengthwise axis of the first member 15'. The inside diameter 65' is greater than the inside diameter 75' of the first lumen 62'. The recess 64' is sized and configured to receive the protuberance 112' defined by the second member 17', as described herein. The inside diameter 65' of the recess 62' is equal to the inside diameter 117' of the protuberance 112' and the length 67' of the recess 64' is equal to the thickness 119' of the protuberance 112'. This configuration provides a mechanism to releasably attach the first member 15' to the second member 17' using a snap fit connection between the first member 15' and the second member 17'. However, alternative embodiments can include a recess that has an inside diameter that is greater than, substantially equal to, or less than the outside diameter of a protuberance and/or a recess that has a length that is greater than, substantially equal to, or less than the thickness of the protuberance. Alternatively, a first member can define a protuberance and a second member can define a recess.

Threads 70' extend from the distal end 58' toward the proximal end 56' and are disposed distal to the port 66'. Threads 70' have a helical configuration that is sized and configured to interact with the helical configuration defined by the threads defined by a cap (e.g., cap 18). For example, the threads 70' defined by the first member 15' are sized and configured to mate with the threads defined by a cap such that the first member 15' is releasably attached to the cap using threads 70' and the threads defined by the cap. Threads 70' provide a mechanism to releasably attach a cap to the first member 15'. Alternative embodiments can include threads that extend between the proximal end and the distal end of a first member.

The first member 15' can be formed of any suitable material. Skilled artisans will be able to select a suitable material to form the first member of an intermediate member according to a particular embodiment based on various considerations, including the material(s) that forms an elongate member, sheath, cap, and/or a second member included in a medical device of which the first member is a component. Example materials considered suitable to form a first member include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular application. In the illustrated embodiment, the first member 15' is formed of acrylonitrile butadiene styrene (ABS).

In the illustrated embodiment, the second member 17' comprises a proximal end 102', a distal end 104', and a body 106'. The second member 17' has a length 107', an outside diameter 109', and an inside diameter 111'. The length 107' extends from the proximal end 102' to the distal end 104' of the second member 17'. The outside diameter 109' is greater than the first outside diameter of the proximal portion of an elongate member. The body 106' of the second member 17' defines a lumen 108', a recess 110', and a protuberance 112'.

The lumen 108' extends from a first opening 114' defined on the proximal end 102' of the second member 17' to a second opening 116' defined on the distal end 104' of the second member 17'. Each of the lumen 108', first opening 114', and second opening 116' has an inside diameter that is sized and configured to receive the shaft of an elongate member. In the illustrated embodiment, each of the first lumen 108', first opening 114', and second opening 116' has an inside diameter 111' that is less than the first outside diameter of the proximal portion of an elongate member and greater than the first outside diameter of a shaft. However, other inside diameters are considered suitable for each of the first lumen, first opening, and second opening, such as inside diameters that are less than, equal to, substantially equal to, or greater than the diameters of other features described herein (e.g., outside diameter of a shaft).

The recess 110' is defined between the proximal end 102' and the distal end 104' of the second member 17' within the lumen 108' and has an inside diameter 113' and a length 115'. The recess 110' extends from the inner surface of the second member 17' and away from the lengthwise axis of the second member 17'. The inside diameter 113' is greater than the inside diameter 111' of the lumen 108'. The recess 110' is sized and configured to receive the protuberance defined by an elongate member (e.g., protuberance 48). The inside diameter 113' of the recess 110' can be equal to, substantially equal to, greater than, or less than the outside diameter of the protuberance defined by an elongate member. The length 115' of the recess 110' can be equal to, substantially equal to, greater than, or less than the thickness of the protuberance defined by an elongate member. For example, the recess can have an inside diameter that is equal to the diameter defined by a protuberance and can have a length that is equal to the length of a protuberance. This configuration provides a mechanism to releasably attach the second member 17' to an elongate member using a snap fit connection between the second member 17' and the elongate member. Alternatively, an elongate member can define a recess and an intermediate member can define a protuberance.

The protuberance 112' is defined between the proximal end 102' and the distal end 104' of the second member 17' within lumen 108'. The protuberance 112' extends from the inner surface of the second member 17' and toward the lengthwise axis of the second member 17'. The protuberance 112' has an inside diameter 117' and a thickness 119'. The inside diameter 117' of the protuberance 112' is less than the inside diameter 111' of lumen 108'. The thickness 119' of the protuberance 112' extends from the proximal end of the protuberance 112' to the distal end of the protuberance 112' and can be any suitable thickness capable of releasably attaching the second member 17' to the first member 15'.

The second member 17' can be formed of any suitable material. Skilled artisans will be able to select a suitable material to form a second member according to a particular embodiment based on various considerations, including the material(s) that forms an elongate member, sheath, cap, and/or a first member included in a medical device of which the second member is a component. Example materials considered suitable to form a second member include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, polyetheretherketone (PEEK), silicone, acrylonitrile butadiene styrene (ABS), polyoxymethylene (e.g., acetal), and any other material considered suitable for a particular application. In the illustrated embodiment, the second member 17' is formed of high-density polyethylene (HDPE). Optionally, the second member can be formed of a material that is the same as, or different than, the material that forms an elongate member (e.g., elongate member 12).

Any suitable locking structure can be included on a first member 15' and/or second member 17' to provide releasable attachment between the second member 17' and an elongate member and between the first member 15' and the second member 17'. Skilled artisans will be able to select a suitable locking structure to include on a first member and/or a second member according to a particular embodiment based on various considerations, including the material(s) that forms the elongate member, first member, and/or second member. Example locking structures considered suitable between an elongate member and a second member and/or between a first member and a second member include interlocking structures, structures that provide a friction fit between the elongate member and the intermediate member, morse taper configurations, threaded connections, mechanical fasteners, and any other structure considered suitable for a particular embodiment.

In use, the first portion 15' is attached to the second portion 17' such that protuberance 112' is disposed within recess 64'. The shaft of an elongate member is passed through the lumen 108' of the second member 17' and through the lumen 62' of the first member 15' such that the protuberance defined by the elongate member is disposed within the recess 110' defined by the second member 17'. Depending on the structural configuration of the recess defined by a first member 15' and/or the recess defined by a second member 17', alternative embodiments can include a protuberance that is entirely, or partially, disposed within a recess.

While the intermediate member 14' has been illustrated as having a particular structural arrangement, an intermediate member can have any suitable structural arrangement. Skilled artisans will be able to select a suitable structural arrangement for an intermediate member according to a particular embodiment based on various considerations, including the structural arrangement of an elongate member, sheath, and/or cap included in a medical device of which the intermediate member is a component. Example structural arrangements considered suitable for an intermediate member include intermediate members that omit the inclusion of a port, intermediate members that omit the inclusion of a recess, and any other structural arrangement considered suitable for a particular application.

Any of the components described herein, such as the elongate members, intermediate members, sheaths, and/or caps, can be interchangeable with the other components described herein. For example, intermediate member 14' can be included in medical device 10 alternative to intermediate member 14. In these embodiments, the recess defined by the second portion can be sized and configured to receive the protuberance defined by the shaft and the threads defined on the intermediate member can optionally be disposed on a portion of the intermediate member that is disposed between the tapered portion and the proximal portion of the intermediate member or such that they extend from the distal end of the intermediate member toward the proximal end of the intermediate member and beyond the tapered portion of the intermediate member. Alternatively, intermediate member 14' can be included in medical device 410 alternative to cap 418. In these embodiments, the recess defined by the second portion can be sized and configured to receive the protuberance defined by the shaft and the intermediate member can optionally omit the inclusion of threads.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A medical device comprising:
    an elongate member having a first proximal end, a first distal end, a proximal portion and a shaft extending from the proximal portion, the proximal portion having a first outside diameter, the shaft having a second proximal end attached to the proximal portion and a second distal end, the shaft having a second outside diameter that is less than the first outside diameter of the proximal portion;
    an intermediate member releasably attached to the elongate member and releasably disposed on the shaft, the intermediate member having a third proximal end disposed between the first proximal end and the first distal end, a third distal end, a third outside diameter, and an intermediate member body defining an intermediate member lumen, the third outside diameter being greater than the first outside diameter of the proximal portion, the intermediate member lumen having a first inside diameter that is less than the first outside diameter of the proximal portion;
    a cap releasably attached to the intermediate member and releasably disposed on the shaft, the cap having a third fourth proximal end, a fourth distal end, and a cap body defining a cap lumen; and
    a sheath partially disposed between the intermediate member and the cap and disposed on the shaft, the sheath having a fifth proximal end, a fifth distal end, and a sheath body defining a first sheath opening on the fifth proximal end of the sheath, a second sheath opening on the fifth distal end of the sheath, and a sheath lumen extending from the first sheath opening to the second sheath opening, the first sheath opening having a second inside diameter that is greater than the first inside diameter of the intermediate member lumen.

2. The medical device of claim 1, wherein the intermediate member has an outer surface having a first tapered portion, the first tapered portion of the intermediate member disposed within the sheath lumen.

3. The medical device of claim 2, wherein the sheath has a tapered proximal portion;
wherein the cap has an inner surface having a second tapered portion; and
wherein the sheath contacts the first tapered portion of the intermediate member and the second tapered portion of the cap.

4. The medical device of claim 1, wherein the cap is formed of a first material;
wherein the sheath is formed of a second material; and
wherein the second material is relatively more flexible than the first material.

5. The medical device of claim 1, wherein the cap is formed of a first material having a first durometer hardness;
wherein the sheath is formed of a second material having a second durometer hardness; and
wherein the first durometer hardness is greater than the second durometer hardness.

6. The medical device of claim 1, wherein the intermediate member has an outer surface and the intermediate member body defines threads on the outer surface; and
wherein the cap has an inner surface and the cap body defines threads on the inner surface, the threads defined by the cap body sized and configured to mate with the threads defined by the intermediate member body.

7. The medical device of claim 1, wherein the intermediate member has a lengthwise axis and an outer surface, the intermediate member having a protuberance on the outer surface that extends away from the lengthwise axis of the intermediate member, the protuberance defined between the third proximal end and the third distal end;
wherein the cap has a lengthwise axis and an inner surface, the cap body defining a recess on the inner surface that extends away from the lengthwise axis of the cap, the recess defined between the fourth proximal end and the fourth distal end; and
wherein the protuberance defined by the intermediate member is disposed within the recess defined by the cap.

8. The medical device of claim 1, wherein the intermediate member body defines a second intermediate member lumen disposed between the third proximal end and the third distal end, the second intermediate member lumen in fluid communication with the intermediate member lumen.

9. The medical device of claim 1, wherein the intermediate member has a lengthwise axis and an inner surface, the intermediate member body defining a recess on the inner surface that extends away from the lengthwise axis of the intermediate member;
wherein the shaft has a lengthwise axis and an outer surface, the shaft having a protuberance on the outer surface that extends away from the lengthwise axis of the shaft, the protuberance disposed between the second proximal end and the second distal end; and
wherein the protuberance of the shaft is disposed within the recess defined by the intermediate member.

10. The medical device of claim 1, wherein the shaft has a first length extending from the second proximal end to the second distal end;
wherein the sheath has a second length extending from the fifth proximal end to the fifth distal end; and
wherein the first length of the shaft is greater than the second length of the sheath.

11. The medical device of claim 1, wherein the sheath is a tubular member.

12. A medical device comprising:
an elongate member having a first proximal end, a first distal end, a proximal portion and a shaft extending from the proximal portion, the proximal portion having a first outside diameter, the shaft having a second proximal end attached to the proximal portion and a second distal end, the shaft having a second outside diameter that is less than the first outside diameter of the proximal portion;
an intermediate member releasably attached to the elongate member and releasably disposed on the shaft, the intermediate member having a third proximal end disposed between the first proximal end and the first distal end, a third distal end, a third outside diameter, an outer surface, and an intermediate member body defining an intermediate member lumen, the third outside diameter being greater than the first outside diameter of the proximal portion, the outer surface having a first tapered portion, the intermediate member lumen having a first inside diameter that is less than the first outside diameter of the proximal portion;
a cap releasably attached to the intermediate member and releasably disposed on the shaft, the cap having a fourth proximal end, a fourth distal end, an inner surface, and a cap body defining a cap lumen, the inner surface having a second tapered portion, the cap formed of a first material; and
a sheath disposed between and contacting the first tapered portion of the intermediate member and the second tapered portion of the cap, the sheath disposed on the shaft and having a fifth proximal end, a fifth distal end, a tapered proximal portion, and a sheath body defining a first sheath opening on the fifth proximal end of the sheath, a second sheath opening on the fifth distal end of the sheath, and a sheath lumen extending from the first sheath opening to the second sheath opening, the first sheath opening having a second inside diameter that is greater than the first inside diameter of the intermediate member lumen, the sheath formed of a second material;
wherein the first tapered portion of the intermediate member is disposed within the sheath lumen; and
wherein the second material is relatively more flexible than the first material.

13. The medical device of claim 12, wherein the first material has a first durometer hardness;
wherein the second material has a second durometer hardness; and
wherein the first durometer hardness is greater than the second durometer hardness.

14. The medical device of claim 12, wherein the intermediate member body defines threads on the outer surface; and
wherein the cap body defines threads on the inner surface, the threads defined by the cap body sized and configured to mate with the threads defined by the intermediate member body.

15. The medical device of claim 12, wherein the intermediate member has a lengthwise axis, the intermediate member having a protuberance on the outer surface that extends away from the lengthwise axis of the intermediate member, the protuberance defined between the third proximal end and the third distal end;
   wherein the cap has a lengthwise axis, the cap body defining a recess on the inner surface that extends away from the lengthwise axis of the cap, the recess defined between the fourth proximal end and the fourth distal end; and
   wherein the protuberance defined by the intermediate member is disposed within the recess defined by the cap.

16. The medical device of claim 12, wherein the intermediate member body defines a second intermediate member lumen disposed between the third proximal end and the third distal end, the second intermediate member lumen in fluid communication with the intermediate member lumen.

17. The medical device of claim 12, wherein the intermediate member has a lengthwise axis and an inner surface, the intermediate member body defining a recess on the inner surface that extends away from the lengthwise axis of the intermediate member;
   wherein the shaft has a lengthwise axis and an outer surface, the shaft having a protuberance on the outer surface that extends away from the lengthwise axis of the shaft, the protuberance disposed between the second proximal end and the second distal end; and
   wherein the protuberance of the shaft is disposed within the recess defined by the intermediate member.

18. The medical device of claim 12, wherein the shaft has a first length extending from the second proximal end to the second distal end;
   wherein the sheath has a second length extending from the fifth proximal end to the fifth distal end; and
   wherein the first length of the shaft is greater than the second length of the sheath.

19. The medical device of claim 12, wherein the sheath is a tubular member.

20. A medical device comprising:
   an elongate member having a first proximal end, a first distal end, a proximal portion and a shaft extending from the proximal portion, the proximal portion having a first outside diameter, the shaft having a lengthwise axis, a second proximal end attached to the proximal portion, a second distal end, an outer surface, and a protuberance, the shaft having a second outside diameter that is less than the first outside diameter of the proximal portion, the protuberance disposed on the outer surface of the shaft and extending away from the lengthwise axis of the shaft, the protuberance disposed between the second proximal end and the second distal end;
   an intermediate member releasably attached to the elongate member and releasably disposed on the shaft, the intermediate member having a lengthwise axis, a third proximal end disposed between the first proximal end and the first distal end, a third distal end, a third outside diameter, an outer surface, an inner surface, and an intermediate member body defining an intermediate member lumen, threads, and a recess, the third outside diameter being greater than the first outside diameter of the proximal portion, the outer surface having a first tapered portion, the intermediate member lumen having a first inside diameter that is less than the first outside diameter of the proximal portion, the threads of the intermediate member defined on the outer surface of the intermediate member, the recess defined on the inner surface and extending away from the lengthwise axis of the intermediate member;
   a cap releasably attached to the intermediate member and releasably disposed on the shaft, the cap having a fourth proximal end, a fourth distal end, an inner surface, and a cap body defining a cap lumen and threads, the inner surface having a second tapered portion, the cap formed of a first material, the threads of the cap defined on the inner surface of the cap, the threads of the cap sized and configured to mate with the threads defined by the intermediate member body; and
   a sheath disposed between and contacting the first tapered portion of the intermediate member and the second tapered portion of the cap, the sheath disposed on the shaft and having a fifth proximal end, a fifth distal end, a tapered proximal portion, and a sheath body defining a first sheath opening on the fifth proximal end of the sheath, a second sheath opening on the fifth distal end of the sheath, and a sheath lumen extending from the first sheath opening to the second sheath opening, the first sheath opening having a second inside diameter that is greater than the first inside diameter of the intermediate member lumen, the sheath formed of a second material;
   wherein the first tapered portion of the intermediate member is disposed within the sheath lumen;
   wherein the second material is relatively more flexible than the first material; and
   wherein the protuberance of the shaft is disposed within the recess defined by the intermediate member.

* * * * *

UNITED STATES PATENT AND TRADEMARK OFFICE
CERTIFICATE OF CORRECTION

PATENT NO. : 9,974,563 B2  
APPLICATION NO. : 14/721618  
DATED : May 22, 2018  
INVENTOR(S) : Darin Schaeffer, Kathryn Hardert and Joshua Haines It is certified that error appears in the above-identified patent and that said Letters Patent is hereby corrected as shown below:

In the Claims

Claim 1, at Column 36, Lines 61 through 64, reads:
"a cap releasably attached to the intermediate member and releasably disposed on the shaft, the cap having a third fourth proximal end, a fourth distal end, and a cap body defining a cap lumen; and".

Should read:
--a cap releasably attached to the intermediate member and releasably disposed on the shaft, the cap having a fourth proximal end, a fourth distal end, and a cap body defining a cap lumen; and--.

Signed and Sealed this  
Tenth Day of July, 2018

Andrei Iancu  
*Director of the United States Patent and Trademark Office*